US012623082B2

(12) United States Patent
Molina et al.

(10) Patent No.: US 12,623,082 B2
(45) Date of Patent: May 12, 2026

(54) STIMULATION PATTERNS FOR DEEP BRAIN STIMULATION

(71) Applicant: Medtronic, Inc., Minneapolis, MN (US)

(72) Inventors: Rene A. Molina, Maple Grove, MN (US); Abbey Beuning Holt Becker, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 592 days.

(21) Appl. No.: 17/934,360

(22) Filed: Sep. 22, 2022

(65) Prior Publication Data

US 2023/0110685 A1     Apr. 13, 2023

Related U.S. Application Data

(60) Provisional application No. 63/252,357, filed on Oct. 5, 2021.

(51) Int. Cl.
*A61N 1/36* (2006.01)

(52) U.S. Cl.
CPC ..... *A61N 1/36178* (2013.01); *A61N 1/36135* (2013.01); *A61N 1/36171* (2013.01); *A61N 1/36067* (2013.01)

(58) Field of Classification Search
CPC .............. A61N 1/0534; A61N 1/36139; A61N 1/36135; A61N 1/3614; A61N 1/36182;
(Continued)

(56)     References Cited

U.S. PATENT DOCUMENTS 7,050,856 B2    5/2006   Stypulkowski
7,117,034 B2   10/2006   Kronberg
(Continued)

OTHER PUBLICATIONS

"Unilateral Conditional Dorsal Genital Nerve Stimulation to Suppress Neurogenic Detrusor Overactivity Using a Needle Electrode," International Continence Society Abstract, 39th Annual Meeting of the ICS, San Francisco, CA, USA, Sep. 29 through Oct. 3, 2009, 2 pp.

(Continued)

*Primary Examiner* — Benjamin J Klein
*Assistant Examiner* — Daniel Tehrani
(74) *Attorney, Agent, or Firm* — Shumaker & Sieffert, P.A.

(57)     ABSTRACT

This disclosure is directed to devices, systems, and techniques for delivering electrical stimulation. In some examples, a system includes processing circuitry configured to: receive information representative of a bioelectric brain signal recorded from a brain of a patient; and determine, based on the information, at least one pathological frequency of the bioelectric brain signal. Additionally, the processing circuitry is configured to select, based on the at least one pathological frequency, a sequence of pulse bursts at a pulse burst frequency, the sequence of pulse bursts at least partially defining electrical stimulation deliverable to an area of a brain of a patient, wherein adjacent pulse bursts within the sequence comprise different intra-burst pulse frequencies; and control a medical device to deliver the electrical stimulation comprising the sequence of pulse bursts to the area of the brain of the patient.

20 Claims, 9 Drawing Sheets

(58) Field of Classification Search

CPC .......... A61N 1/36185; A61N 2001/083; A61N 1/36178; A61N 1/36171; A61N 1/36067; A61N 1/3606; A61N 1/36189; A61N 1/0531; A61N 1/36082; A61N 1/37235

See application file for complete search history.

(56) References Cited

U.S. PATENT DOCUMENTS

| | | |
|---|---|---|
| 7,734,340 B2 | 6/2010 | De Ridder |
| 8,825,166 B2 | 9/2014 | John |
| 9,168,374 B2 | 10/2015 | Su |
| 9,833,622 B2 | 12/2017 | Moffitt et al. |
| 2004/0147976 A1 | 7/2004 | Gordon et al. |
| 2006/0015153 A1 | 1/2006 | Gliner et al. |
| 2007/0135860 A1 | 6/2007 | Tass |
| 2009/0222058 A1 | 9/2009 | Craggs |
| 2012/0197336 A1 | 8/2012 | Su |
| 2018/0085585 A1 | 3/2018 | Stanslaski et al. |
| 2018/0110991 A1* | 4/2018 | Molnar ................. G16H 20/30 |
| 2018/0193653 A1 | 7/2018 | Bokil |
| 2019/0290912 A1 | 9/2019 | Raike et al. |
| 2020/0338353 A1 | 10/2020 | Jackson et al. |

OTHER PUBLICATIONS

Amir et al., "Burst Discharge in Primary Sensory Neurons: Triggered by Subthreshold Oscillations, Maintained by Depolorizing Afterpotentials," The Journal of Neuroscience, vol. 22(3), Feb. 2002, 12 pp.

Bruns et al., "Intraurethral Stimulation for Reflex Bladder Activation Depends on Stimulation Pattern and Location," Neurourology and Urodynamics, Aug. 2009, pp. 561-566.

Su et al., "Effects of Opiods on Mechanosensitive Pelvic Nerve Afferent Fibers Innervating the Urinary Bladder of the Rat," Journal of Neurophisiology, vol. 77, Mar. 1997, pp. 1566-1580.

Su et al., "Mechanosensitive Pelvic Nerve Afferent Fibers Innervating the Colon of the Rat Are Polymodal in Character," Journal of Neurophysiology, vol. 80, Nov. 1998, pp. 2632-2644.

Su et al., "The Effect of Amitriptyline on Ectopic Discharge of Primary Afferent Fibers in the L5 Dorsal Root in a Rat Model of Neuropathic Pain," Anesthesia & Analgesia, vol. 108(5), May 2009, 9 pp.

International Search Report and Written Opinion of International Application No. PCT/IB2022/059294 dated Dec. 14, 2022, 12 pp.

* cited by examiner

802
CONTROL A MEDICAL DEVICE TO DELIVER ONE OR MORE SEQUENCES OF PULSE BURSTS TO AN AREA OF A BRAIN OF A PATIENT IN ORDER TO SUPPRESS ONE OR MORE PATHOLOGICAL BRAIN SIGNALS

804
CONTROL THE MEDICAL DEVICE TO CEASE DELIVERING THE ONE OR MORE SEQUENCES OF PULSE BURSTS

STIMULATION PATTERNS FOR DEEP BRAIN STIMULATION

This application claims the benefit of U.S. Provisional Patent Application No. 63/252,357, filed on Oct. 5, 2021, the entire content of which is incorporated herein by reference.

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Patients afflicted with movement disorders or other neurodegenerative impairment, whether by disease or trauma, may experience muscle control and movement problems, such as rigidity, bradykinesia (i.e., slow physical movement), rhythmic hyperkinesia (e.g., tremor), nonrhythmic hyperkinesia (e.g., tics) or akinesia (i.e., a loss of physical movement). Movement disorders may be found in patients with Parkinson's disease, multiple sclerosis, and cerebral palsy, among other conditions. Delivery of electrical stimulation and/or a fluid (e.g., a pharmaceutical drug) by a medical device to one or more sites in a patient, such as a brain, spinal cord, leg muscle or arm muscle, in a patient may help alleviate, and in some cases, eliminate symptoms associated with movement disorders.

SUMMARY

In general, the disclosure is directed to devices, systems, and techniques for delivering electrical stimulation to the brain of a patient to suppress bioelectric brain signals in an area of the patient's brain. In some examples, the bioelectric brain signals of a patient may oscillate at a frequency that may be referred to as a pathological frequency of the patient because it is associated with symptoms that do not occur during normal physiologic frequencies. When the biological brain signals of the patient oscillate at such a pathological frequency, a medical device may deliver electrical stimulation to an area of the patient's brain to disrupt or desynchronize this pathological frequency, for example. The electrical stimulation may include a predetermined or dynamic sequence of pulse bursts. The medical device may deliver the sequence of pulse bursts to evoke synaptic depression without entraining a larger network of bioelectric brain signals. When the medical device evokes synaptic depression, the medical device may suppress the pathological brain signals such that the pathological brain signal are attenuated or completely eliminated, which results in reduced or eliminated symptoms associated with the pathological brain signals.

In some examples, a system includes processing circuitry configured to: receive information representative of a bioelectric brain signal recorded from a brain of a patient; determine, based on the information, at least one pathological frequency of the bioelectric brain signal; select, based on the at least one pathological frequency, a sequence of pulse bursts at a pulse burst frequency, the sequence of pulse bursts at least partially defining electrical stimulation deliverable to an area of a brain of a patient, wherein adjacent pulse bursts within the sequence comprise different intra-burst pulse frequencies; and control a medical device to deliver the electrical stimulation comprising the sequence of pulse bursts to the area of the brain of the patient.

In some examples, a method includes receiving, by processing circuitry, information representative of a bioelectric brain signal recorded from a brain of a patient; determining, by the processing circuitry and based on the information, at least one pathological frequency of the bioelectric brain signal; selecting, by processing circuitry and based on the at least one pathological frequency, a sequence of pulse bursts at a pulse burst frequency, the sequence of pulse bursts at least partially defining electrical stimulation deliverable to an area of a brain of a patient, wherein adjacent pulse bursts within the sequence comprise different intra-burst pulse frequencies; and controlling, by the processing circuitry, a medical device to deliver the electrical stimulation comprising the sequence of pulse bursts to the area of the brain of the patient.

In some examples, a computer-readable medium includes instructions that, when executed by a processor, causes the processor to: receive information representative of a bioelectric brain signal recorded from a brain of a patient; determine, based on the information, at least one pathological frequency of the bioelectric brain signal; select, based on the at least one pathological frequency, a sequence of pulse bursts at a pulse burst frequency, the sequence of pulse bursts at least partially defining electrical stimulation deliverable to an area of a brain of a patient, wherein adjacent pulse bursts within the sequence comprise different intra-burst pulse frequencies; and control a medical device to deliver the electrical stimulation comprising the sequence of pulse bursts to the area of the brain of the patient.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
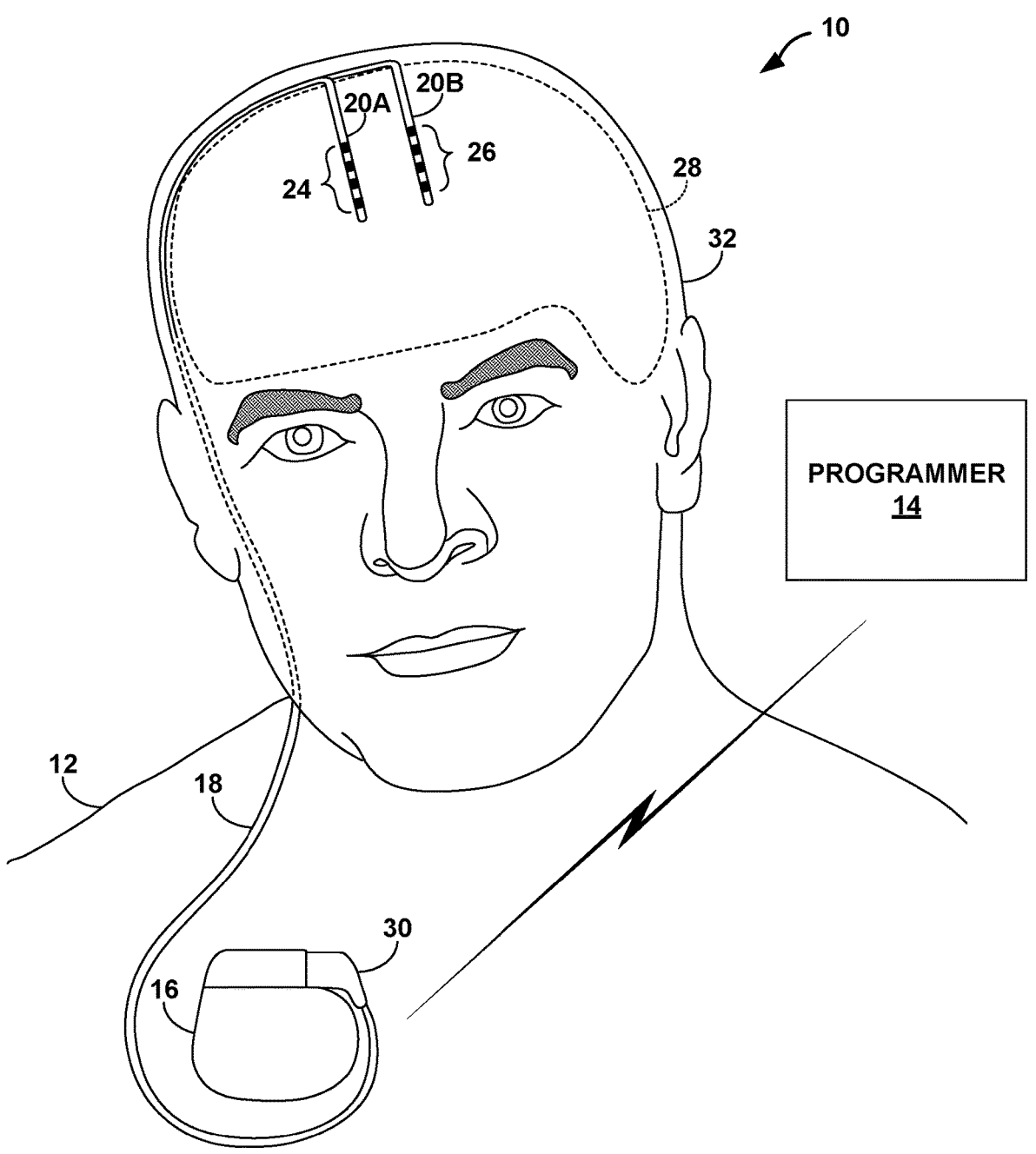
FIG. 1 is a conceptual diagram illustrating an example system for delivering electrical stimulation to a patient, in accordance with one or more techniques of this disclosure.

The disclosure describes examples of medical devices, systems, and techniques for delivering electrical stimulation to the brain of a patient in order to suppress one or more bioelectric brain signals of the patient. In some examples, the bioelectric brain signals may oscillate at a frequency that corresponds to pathological brain signals of the patient. Pathological brain signals can cause undesirable symptoms such as rigidity, akenesia, bradykinesia, diskensia, and/or resting tremor. Consequently, it may be beneficial to suppress these pathological brain signals without disrupting other, normal or nonpathological, brain functions of the patient. The medical device may detect pathological brain signals in an area of the patient's brain and deliver electrical stimulation to the area of the patient's brain. The medical device may deliver the electrical stimulation to evoke synaptic depression in the area of the patient's brain without entraining a larger network of bioelectric brain signals. When the medical device evokes synaptic depression, the medical device may suppress the pathological brain signals such that an effect of the pathological brain signals on the patient is attenuated or completely eliminated.

As will be described further below, in some examples, a medical device may deliver electrical stimulation to the brain of the patient to manage or otherwise treat a patient disorder. In some examples, the oscillation of bioelectric brain signals at a particular frequency or frequency band or range may be associated with one or more symptoms of a patient disorder. These oscillations may be referred to as pathological signals or pathological frequencies. For example, bioelectric brain signals oscillating in the particular frequency range may be associated with one or more symptoms of a patient disorder in the sense that such symptoms frequently occur or manifest themselves when the bioelectric brain signals oscillate at such a frequency range. Such occurrences may be a result of the brain signal oscillations within one or more regions of the brain of a patient interfering with the normal function of that region of the brain. As used herein, a frequency or range of frequencies may be referred to as a pathological frequency or pathological frequency range when oscillations of brain signals at such frequency or frequencies are associated in such a manner with one or more symptoms of a patient disorder. Similarly, bioelectric brain signals oscillating at one or more pathological frequencies may be referred to as pathological brain signals.

As one example, in the case of Parkinson's disease, beta frequency oscillations (e.g., between approximately 12 Hertz (Hz) to approximately 35 Hz) in the subthalamic nucleus (STN), globus pallidus interna (GPi), globus pallidus externa (GPe), and/or other areas of the basal ganglia may be associated with one or more motor symptoms including, e.g., rigidity, akenesia, bradykinesia, diskensia, and/or resting tremor. These motor symptoms may be associated with bioelectric brain signals oscillating in the beta frequency range in the sense that such symptoms frequently occur when the bioelectric brain signals oscillate within the beta frequency range. Persistence of oscillation in the beta frequency range may result in oscillatory "interference" that can limit the normal functions of the above regions of the brain. Networks of oscillating neurons may be synchronized by electrical and chemical signals that cause the activity of the network to phase lock and resonate at some frequency. In some examples, the symptoms of Parkinson's disease generally manifest themselves in conjunction with the presence of beta frequency range oscillations (e.g., above some threshold activity level). In some examples, the frequency of symptom manifestations may increase in conjunction with the presence of beta frequency range oscillations.

In some examples, one or more symptoms of a patient disorder associated with oscillations of bioelectrical brain activity at a particular frequency or frequency band may be treated by reducing or substantially eliminating bioelectric brain signals at such pathological frequencies when such activity occurs. For example, the manifestation of one or more symptoms associated with bioelectric brain signals with oscillation in the beta frequency range for patients with Parkinson disease may be reduced or substantially eliminated by evoking synaptic depression in an area of the patient's brain where the bioelectric brain signals in the beta frequency range are present. The medical device may evoke synaptic depression by delivering a sequence of pulse bursts to the area of the patient's brain where the bioelectric brain signals in the beta frequency range are present, where the medical device delivers the sequence of pulse bursts at a pulse burst frequency that matches a frequency of the bioelectric brain signals. In some examples, the medical device delivers a pulse burst of the sequence of pulse bursts corresponding to a valley of the bioelectric brain signals. By stimulating the valleys of the bioelectric brain signal, the medical device may suppress the bioelectric brain signal in a local area of the patient's brain without substantially affecting other areas of the brain.

The sequence of pulse bursts may include pulse bursts of varying frequencies. For example, each pulse burst of the sequence of pulse bursts may include a set of pulses having an intra-burst pulse frequency, where the intra-burst pulse frequency of one pulse burst may be different than the intra-burst pulse frequencies of one or more other pulse bursts of the sequence of pulse bursts. It may be beneficial for the intra-burst pulse frequency of a pulse burst to be different than the intra-burst pulse frequencies of adjacent pulse bursts in the sequence of pulse bursts. Moreover, it may be beneficial for adjacent pulse bursts to be nonharmonic in frequency in order to prevent the sequence of pulse bursts from entraining the bioelectric brain signals. That is, a factor of the intra-burst pulse frequency of one pulse burst may be different than the factors of the intra-burst pulse frequencies of adjacent pulse bursts of the sequence of pulse bursts. When the medical device delivers a sequence of pulse bursts where adjacent pulse bursts have nonharmonic frequencies, the medical device may suppress bioelectric brain signals oscillating at a frequency matching the pulse burst frequency in which the medical device delivers the pulse bursts. However, the medical device may avoid entraining the bioelectric brain signals by delivering the pulse bursts at these nonharmonic frequencies and thus affecting bioelectric brain signals across the patient's brain.

The medical device may suppress bioelectric brain signals without entraining the bioelectric brain signals so that electrical stimulation in one area of the brain does not affect brain activity in other areas of the brain as compared with techniques where the medical device does entrain bioelectric brain signals. A bioelectric brain signal may be characterized as being entrained by the delivered electrical stimulation when the bioelectric brain signal is pulled, drawn, or otherwise follows changes in the frequency of the delivered electrical stimulation. Entrainment may be the "following" of period and/or phase changes to delivered electrical stimulation for a period of time, and may include instance in which the changes the bioelectric brain signals are substantially the same as that of the changes to the delivered stimulation and instance in which the changes are not substantially the same but follow to some degree with the changes to the electrical stimulation. When bioelectric brain signals follow a change in the period and/or phase of electrical stimulation in one area of the brain, the period and/or phase of bioelectric brain signals in other areas may also follow the change. In some examples, entrainment of bioelectric brain signals by the delivered electrical stimulation may be evidenced by an oscillation frequency of the brain signals that matches the frequency of the electrical stimulation and a constant phase relationship between the brain signal oscillations and the delivered electrical stimulation. In some cases, it may be beneficial to avoid entrainment of biological brain signals in order to deliver therapy without causing broad changes in brain activity.

In some examples, the medical device may deliver the sequence of pulse bursts at a pulse burst frequency which is substantially the same frequency as that of bioelectric brain signal oscillations. As described herein, the term "pulse burst frequency" refers to the frequency at which the medical device delivers the sequence of pulse bursts. For example, when the medical device delivers the sequence of pulse bursts at 20 Hz, the medical device delivers the sequence of pulse bursts at a rate of 20 pulse bursts per second. In other examples, the sequence of pulse bursts may be delivered at some multiple (approximately 2 times, approximately 3 times, and/or approximately 0.5 times) of bioelectric brain signal oscillations. By delivering the sequence of pulse bursts with a frequency that is substantially the same as that of the brain signal oscillation frequency or at substantially the same frequency as a whole multiple of the oscillation frequency (e.g., approximately 2 times, approximately 3 times, and so forth), each pulse burst of the sequence of pulse bursts may correspond to a respective event of the bioelectric brain signal. In some examples, each pulse burst of the sequence of pulse bursts corresponds to a respective peak of the bioelectric brain signal. In one example, a start of each pulse burst of the sequence of pulse bursts may occur at a respective peak of the bioelectrical signal. In another example, a midpoint of each pulse burst of the sequence of pulse bursts may occur at a respective peak of the bioelectrical signal. In some examples, each pulse burst of the sequence of pulse bursts corresponds to a respective valley of the bioelectric brain signal. In one example, a start of each pulse burst of the sequence of pulse bursts may occur at a respective valley of the bioelectric signal. In another example, a midpoint of each pulse burst of the sequence of pulse bursts may occur at a respective valley of the bioelectrical signal. When each pulse burst of the sequence of pulse bursts corresponds to a respective valley of the bioelectric brain signal, the sequence of pulse bursts may suppress the bioelectric brain signal such that one or more symptoms caused by the bioelectric brain signal are attenuated or completely eliminated.

In other examples, the medical device may deliver the sequence of pulse bursts at some frequency that is a fraction (½ or ¼, for example) of the brain signal oscillation frequency. In such a case, each pulse burst of the sequence of pulse bursts might not match substantially all peaks or substantially all valleys of the bioelectric brain signal at the given oscillation frequency. However, the sequence of pulse bursts may match a fraction of the peaks of the brain signal or a fraction of the valleys of the brain signal (e.g., approximately 50 percent for stimulation at a frequency approximately one half of the oscillation frequency).

In some examples, such electrical stimulation therapy may be delivered to the brain of the patient in response to detecting the bioelectric brain signal oscillations at a pathological frequency and/or the detection of manifestations of one or more motor symptoms associated with the pathological frequency. Additionally, or alternatively, such electrical stimulation therapy may be periodically delivered to the brain of a patient and not in response to the detection of oscillations at a pathological frequency and/or the detection of manifestations of one or more motor symptoms associated with the pathological frequency. In some examples, the electrical stimulation therapy may be delivered in response to patient input. In some examples, the electrical stimulation may be continuously delivered to the patient.

FIG. 1 is a conceptual diagram illustrating an example system 10 for delivering electrical stimulation to a patient 12, in accordance with one or more techniques of this disclosure. In FIG. 1, the system 10 may deliver electrical stimulation therapy to treat or otherwise manage a patient condition, such as, e.g., a movement disorder of the patient 12. One example of a movement disorder treated by the system 10 may include Parkinson's disease. The patient 12 ordinarily will be a human patient. In some cases, however, the system 10 may be applied to other mammalian or non-mammalian non-human patients.

For ease of illustration, examples of the disclosure will primarily be described with regard to the treatment of movement disorders and, in particular, the treatment of Parkinson's disease, e.g., by reducing or preventing the manifestation of symptoms exhibited by patients suffering from Parkinson's disease. As noted above, such symptoms may include rigidity, akenesia, bradykinesia, diskensia, and/or resting tremor. However, the treatment of one or more patient disorders other than that of Parkinson's disease by employing the techniques described herein is contemplated. For example, the described techniques may be employed to manage or other treat symptoms of other patient disorders, such as, but not limited to, psychological disorders, mood disorders, seizure disorders or other neurogenerative impairment. In one example, such techniques may be employed to provide therapy to patient to manage Alzheimer's disease.

The system 10 includes a programmer 14, an implantable medical device (IMD) 16, a lead extension 18, and one or more leads 20A and 20B (collectively "leads 20") with respective sets of electrodes 24, 26. The lead 20A may include the set of electrodes 24, and the lead 20B may include the set of electrodes 26. The IMD 16 includes a stimulation therapy module that includes a stimulation generator that generates and delivers electrical stimulation therapy to one or more regions of a brain 28 of the patient 12 via a subset of the sets of electrodes 24, 26 of the leads 20A and 20B, respectively. In the example shown in FIG. 1, the system 10 may be referred to as a DBS system because the IMD 16 provides electrical stimulation therapy directly to tissue within the brain 28, e.g., a tissue site under the dura mater of the brain 28. In other examples, the leads 20 may be positioned to deliver therapy to a surface of the brain 28 (e.g., the cortical surface of the brain 28).

In some examples, delivery of stimulation to one or more regions of the brain 28, such as an anterior nucleus (AN), thalamus or cortex of the brain 28, provides an effective treatment to manage a disorder of the patient 12. In some examples, the IMD 16 may provide cortical stimulation therapy to the patient 12, e.g., by delivering electrical stimulation to one or more tissue sites in the cortex of the brain 28. In cases in which the IMD 16 delivers electrical stimulation to the brain 28 to treat Parkinson's disease by modulating brain signals oscillating at pathological frequencies, target stimulation sites may include one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex. Brain signals with oscillations in the beta frequency range may be considered pathological brain signals. As will be described below, the IMD 16 may deliver electrical stimulation selected to entrain the bioelectric brain signals oscillating in the beta frequency range and adjust the frequency of the electrical stimulation to change the oscillation frequency to a higher or lower frequency, e.g., a frequency greater than approximately 40 Hz, such as, e.g., between approximately 40 Hz and approximately 100 Hz or up to approximately 350 Hz. For instances in which the IMD 16 senses the bioelectric brain signals at one or more sites of the brain 28 to detection oscillations at a pathological frequency, the target stimulation site(s) for electrical stimulation delivered to the brain 28 of the patient 12 may be the same and/or different than the sensing site.

In the example shown in FIG. 1, the IMD 16 may be implanted within a subcutaneous pocket above the clavicle of the patient 12. In other examples, the IMD 16 may be implanted within other regions of the patient 12, such as a subcutaneous pocket in the abdomen or buttocks of the patient 12 or proximate the cranium of the patient 12. The lead extension 18 is coupled to the IMD 16 via a connector block 30 (also referred to as a header), which may include, for example, electrical contacts that electrically couple to respective electrical contacts on the lead extension 18. The electrical contacts electrically couple the sets of electrodes 24, 26 carried by the leads 20 to the IMD 16. The lead extension 18 traverses from the implant site of the IMD 16 within a chest cavity of the patient 12, along the neck of the patient 12 and through the cranium of the patient 12 to access the brain 28. Generally, the IMD 16 is constructed of a biocompatible material that resists corrosion and degradation from bodily fluids. The IMD 16 may comprise a housing 34 to substantially enclose components, such as a processor, therapy module, and memory. In some examples, the housing 24 is hermetic.

The leads 20A and 20B may be implanted within the right and left hemispheres, respectively, of the brain 28 in order deliver electrical stimulation to one or more regions of the brain 28, which may be selected based on many factors, such as the type of patient condition for which the system 10 is implemented to manage. Other implant sites for the leads 20 and the IMD 16 are contemplated. For example, the IMD 16 may be implanted on or within a cranium 32 or the leads 20 may be implanted within the same hemisphere or the IMD 16 may be coupled to a single lead that is implanted in one or both hemispheres of the brain 28.

The leads 20 may be positioned to deliver electrical stimulation to one or more target tissue sites within the brain 28 to manage patient symptoms associated with a disorder of the patient 12. The leads 20 may be implanted to position the sets of electrodes 24, 26 at desired locations of the brain 28 through respective holes in the cranium 32. The leads 20 may be placed at any location within the brain 28 such that the sets of electrodes 24, 26 are capable of providing electrical stimulation to target tissue sites within the brain 28 during treatment. For example, in the case of Parkinson's disease, for example, the leads 20 may be implanted to deliver electrical stimulation to one or more basal ganglia sites, including, e.g., subthalamic nucleus (STN), globus pallidus interna (GPi), globus pallidus externa (GPe), pedunculopontine nucleus (PPN), thalamus, substantia nigra pars reticulata (SNr), internal capsule, and/or motor cortex.

Although the leads 20 are shown in FIG. 1 as being coupled to the lead extension 18, in other examples, the leads 20 may be coupled to the IMD 16 via separate lead extensions or directly coupled to the IMD 16. Moreover, although FIG. 1 illustrates the system 10 as including the leads 20A and 20B coupled to the IMD 16 via the lead extension 18, in some examples, the system 10 may include one lead or more than two leads.

The leads 20 may deliver electrical stimulation to treat any number of neurological disorders or diseases in addition to movement disorders, such as seizure disorders or psychiatric disorders. Examples of movement disorders include a reduction in muscle control, motion impairment or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease or Huntington's disease. Examples of psychiatric disorders include MDD, bipolar disorder, anxiety disorders, posttraumatic stress disorder, dysthymic disorder, and OCD. As described above, while examples of the disclosure are primarily described with regard to treating Parkinson's disease, treatment of other patient disorders via delivery of therapy to the brain 28 is contemplated.

The leads 20 may be implanted within a desired location of the brain 28 via any suitable technique, such as through respective burr holes in a skull of the patient 12 or through a common burr hole in the cranium 32. The leads 20 may be placed at any location within the brain 28 such that the sets of electrodes 24, 26 of the leads 20 are capable of providing electrical stimulation to targeted tissue during treatment. Electrical stimulation generated from the stimulation generator (not shown) within the therapy module of the IMD 16 may help prevent the onset of events associated with the patient's disorder or mitigate symptoms of the disorder. For example, electrical stimulation delivered by the IMD 16 to a target tissue site within the brain 28 may include a sequence of pulse bursts delivered at a pulse burst frequency, where the pulse burst frequency of the sequence of pulse bursts matches a pathological frequency of a detected bioelectric brain signal. Although the IMD 16 delivers the sequence of pulse bursts at a consistent pulse burst frequency, the IMD 16 may deliver the pulse bursts themselves at varying frequencies. Delivering a sequence of pulse bursts at a pulse burst frequency when the pulse bursts themselves have varying frequencies may suppress the pathological brain signals without entraining the pathological bran signals. Suppressing a pathological brain signal may mitigate or completely eliminate symptoms associated with the pathological brain signals. In this manner, the IMD 16 may deliver electrical stimulation to reduce or prevent the onset of events associated with the patient's disorder or mitigate symptoms of the disorder.

In the examples shown in FIG. 1, the sets of electrodes 24, 26 of the leads 20 are shown as ring electrodes. Ring electrodes may be relatively easy to program and are typically capable of delivering an electrical field to any tissue adjacent to the leads 20. In other examples, the sets of electrodes 24, 26 of the leads 20 may have different configurations. For example, the sets of electrodes 24, 26 of the leads 20 may have a complex electrode array geometry that is capable of producing shaped electrical fields. The complex electrode array geometry may include multiple electrodes (e.g., partial ring or segmented electrodes) around the perimeter of each of the leads 20, rather than a ring electrode. In this manner, electrical stimulation may be directed to a specific direction from the leads 20 to enhance therapy efficacy and reduce possible adverse side effects from stimulating a large volume of tissue.

In some examples, the housing 34 of the IMD 16 may include one or more stimulation and/or sensing electrodes. For example, the housing 34 can comprise an electrically conductive material that is exposed to tissue of the patient 12 when the IMD 16 is implanted in the patient 12, or an electrode can be attached to the housing 34. In alternative examples, the leads 20 may have shapes other than elongated cylinders as shown in FIG. 1. For example, the leads 20 may be paddle leads, spherical leads, bendable leads, or any other type of shape effective in treating the patient 12.

The IMD 16 may deliver electrical stimulation therapy to the brain 28 of the patient 12 according to one or more stimulation therapy programs. A therapy program may define one or more electrical stimulation parameter values for therapy generated and delivered from the IMD 16 to the brain 28 of the patient 12. Where the IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of the patient 12, the system 10 monitors one or more bioelectric brain signals of the patient 12. For example, the IMD 16 may include a sensing module that senses bioelectric brain signals within one or more regions of the brain 28. In the example shown in FIG. 1, the signals generated by the sets of electrodes 24, 26 are conducted to the sensing module within the IMD 16 via conductors within a respective lead of the leads 20. As described in further detail below, in some examples, a processor of the IMD 16 may sense the bioelectrical signals within the brain 28 of the patient 12 and controls delivery of electrical stimulation therapy to the brain 28 via the sets of electrodes 24, 26 when the bioelectric brain signals are oscillating at a pathological frequency.

In some examples, the sensing module of the IMD 16 may receive the bioelectrical signals from the sets of electrodes 24, 26 or other electrodes positioned to monitored brain signals of the patient 12. The sets of electrodes 24, 26 may also be used to deliver electrical stimulation from the therapy module to target sites within the brain 28 as well as sense brain signals within the brain 28. However, the IMD 16 can also use separate sensing electrodes to sense the bioelectric brain signals. In some examples, the sensing module of the IMD 16 may sense bioelectric brain signals via one or more of the sets of electrodes 24, 26 that are also used to deliver electrical stimulation to the brain 28. In other examples, one or more electrodes of the sets of electrodes 24, 26 may be used to sense bioelectric brain signals while one or more different electrodes of the sets of electrodes 24, 26 may be used to deliver electrical stimulation.

Depending on the particular stimulation electrodes and sense electrodes used by the IMD 16, the IMD 16 may monitor brain signals and deliver electrical stimulation at the same region of the brain 28 or at different regions of the brain 28. In some examples, the electrodes used to sense bioelectric brain signals may be located on the same lead used to deliver electrical stimulation, while in other examples, the electrodes used to sense bioelectric brain signals may be located on a different lead than the electrodes used to deliver electrical stimulation. In some examples, a brain signal of the patient 12 may be monitored with external electrodes, e.g., scalp electrodes. Moreover, in some examples, the sensing module that senses bioelectric brain signals of the brain 28 (e.g., the sensing module that generates an electrical signal indicative of the activity within the brain 28) is in a physically separate housing from the housing 34 of the IMD 16. However, in the example shown in FIG. 1 and the example primarily referred to herein for ease of description, the sensing module and therapy module of the IMD 16 are enclosed within the housing 34.

The bioelectric brain signals monitored by the IMD 16 may reflect changes in electrical current produced by the sum of electrical potential differences across brain tissue. Examples of the monitored bioelectric brain signals include, but are not limited to, an electroencephalogram (EEG) signal, an evoked resonant neural activity (ERNA) signal, an electrocorticogram (ECoG) signal, a local field potential (LFP) sensed from within one or more regions of a patient's brain and/or action potentials from single cells within the patient's brain.

The programmer 14 wirelessly communicates with the IMD 16 as needed to provide or retrieve therapy information. The programmer 14 is an external computing device that the user, e.g., the clinician and/or the patient 12, may use to communicate with the IMD 16. For example, the programmer 14 may be a clinician programmer that the clinician uses to communicate with the IMD 16 and program one or more therapy programs for the IMD 16. Alternatively, the programmer 14 may be a patient programmer that allows the patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to the IMD 16.

The programmer 14 may be a hand-held computing device with a display viewable by the user and an interface for providing input to the programmer 14 (i.e., a user input mechanism). For example, the programmer 14 may include a small display screen (e.g., a liquid crystal display (LCD) or a light emitting diode (LED) display) that presents information to the user. In addition, the programmer 14 may include a touch screen display, keypad, buttons, a peripheral pointing device or another input mechanism that allows the user to navigate through the user interface of the programmer 14 and provide input. If the programmer 14 includes buttons and a keypad, the buttons may be dedicated to performing a certain function, i.e., a power button, or the buttons and the keypad may be soft keys that change in function depending upon the section of the user interface currently viewed by the user.

In some examples, the programmer 14 may be a larger workstation or a separate application within another multifunction device, rather than a dedicated computing device. For example, the multi-function device may be a notebook computer, tablet computer, workstation, cellular phone, personal digital assistant or another computing device that may run an application that enables the computing device to operate as a secure medical device programmer. A wireless adapter coupled to the computing device may enable secure communication between the computing device and the IMD 16.

When the programmer 14 is configured for use by the clinician, the programmer 14 may be used to transmit initial programming information to the IMD 16. This initial information may include hardware information, such as the type of the leads 20, the arrangement of the sets of electrodes 24, 26 on the leads 20, the position of the leads 20 within the brain 28, initial programs defining therapy parameter values, and any other information that may be useful for programming into the IMD 16. The programmer 14 may also be capable of completing functional tests (e.g., measuring the impedance one or more electrodes of the sets of electrodes 24, 26 of the leads 20).

The clinician may also store therapy programs within the IMD 16 with the aid of the programmer 14. During a programming session, the clinician may determine one or more therapy programs that may provide efficacious therapy to the patient 12 to address symptoms associated with the seizure disorder (or another patient condition). For example, the clinician may select one or more electrode combinations with which stimulation is delivered to the brain 28. During the programming session, the patient 12 may provide feedback to the clinician as to the efficacy of the specific program being evaluated or the clinician may evaluate the efficacy based on one or more physiological parameters of patient (e.g., heart rate, respiratory rate or muscle activity). The programmer 14 may assist the clinician in the creation/identification of therapy programs by providing a methodical system for identifying potentially beneficial therapy parameter values.

The programmer 14 may also be configured for use by the patient 12. When configured as a patient programmer, the programmer 14 may have limited functionality (compared to a clinician programmer) in order to prevent the patient 12 from altering critical functions of the IMD 16 or applications that may be detrimental to the patient 12. In this manner, the programmer 14 may only allow the patient 12 to adjust values for certain therapy parameters or set an available range of values for a particular therapy parameter.

The programmer 14 may also provide an indication to the patient 12 when therapy is being delivered, when patient input has triggered a change in therapy or when the power source within the programmer 14 or the IMD 16 needs to be replaced or recharged. For example, the programmer 14 may include an alert LED, may flash a message to the patient 12 via a programmer display, generate an audible sound or somatosensory cue to confirm patient input was received, e.g., to indicate a patient state or to manually modify a therapy parameter.

Whether the programmer 14 is configured for clinician or patient use, the programmer 14 is configured to communicate to the IMD 16 and, optionally, another computing device, via wireless communication. The programmer 14, for example, may communicate via wireless communication with the IMD 16 using radio frequency (RF) telemetry techniques known in the art. The programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. The programmer 14 may also communicate with other programming or computing devices via exchange of removable media, such as magnetic or optical disks, memory cards or memory sticks. Further, the programmer 14 may communicate with the IMD 16 and another programmer via remote telemetry techniques known in the art, communicating via a local area network (LAN), wide area network (WAN), public switched telephone network (PSTN), or cellular telephone network, for example.

The system 10 may be implemented to provide chronic stimulation therapy to the patient 12 over the course of several months or years. However, the system 10 may also be employed on a trial basis to evaluate therapy before committing to full implantation. If implemented temporarily, some components of the system 10 may not be implanted within the patient 12. For example, the patient 12 may be fitted with an external medical device, such as a trial stimulator, rather than the IMD 16. The external medical device may be coupled to percutaneous leads or to implanted leads via a percutaneous extension. If the trial stimulator indicates the system 10 provides effective treatment to the patient 12, the clinician may implant a chronic stimulator within the patient 12 for relatively long-term treatment.

Figure 2:
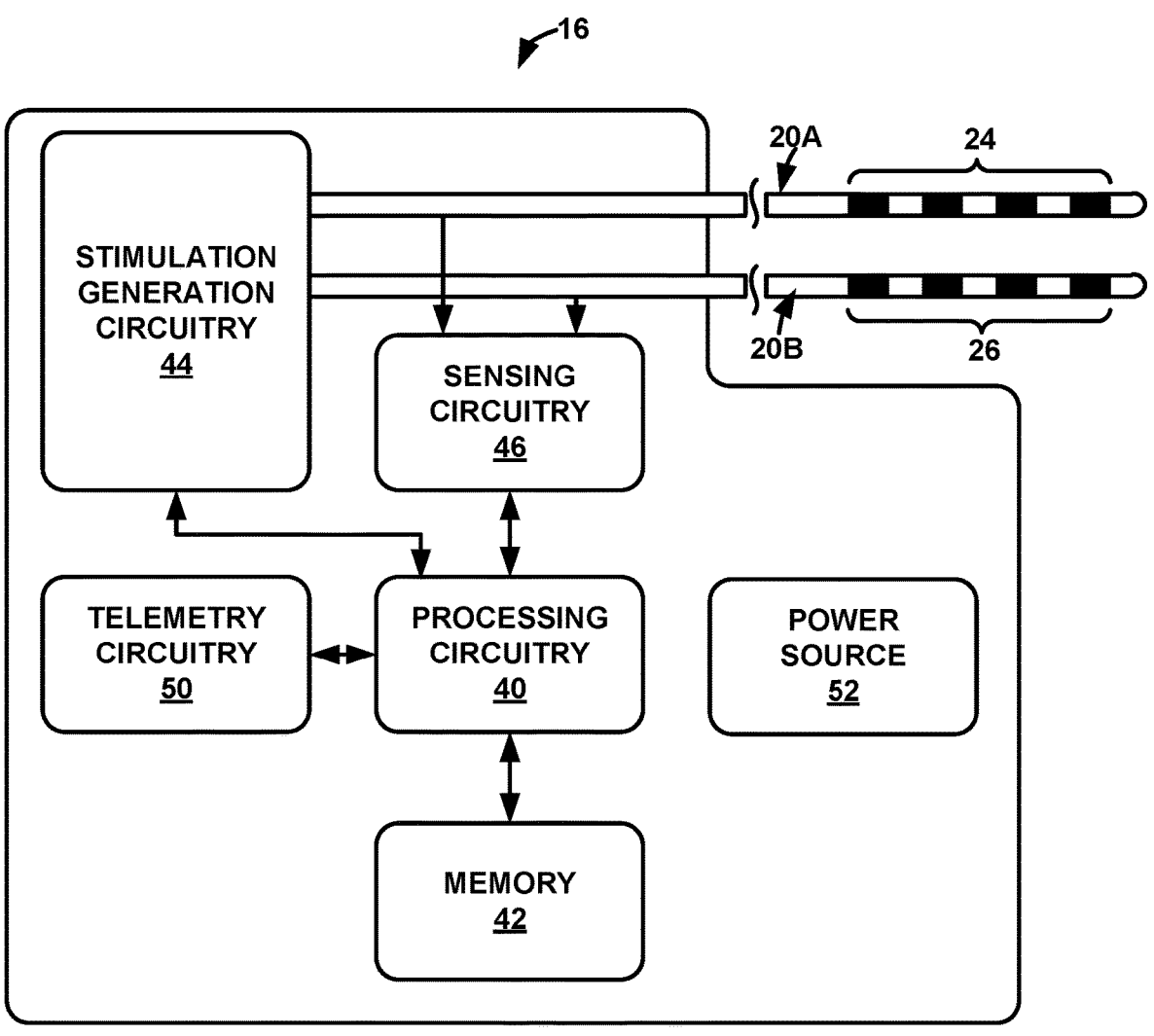
FIG. 2 is a functional block diagram illustrating components of the IMD of FIG. 1, in accordance with one or more techniques of this disclosure.

FIG. 2 is a functional block diagram illustrating components of the IMD 16 of FIG. 1, in accordance with one or more techniques of this disclosure. As seen in FIG. 2, the IMD 16 includes processing circuitry 40, a memory 42, stimulation generation circuitry 44, sensing circuitry 46, telemetry circuitry 50, and a power source 52. The processing circuitry 40 may include any one or more microprocessors, controllers, digital signal processors (DSPs), application specific integrated circuits (ASICs), field-programmable gate arrays (FPGAs), and discrete logic circuitry. The functions attributed to processors described herein, including the processing circuitry 40, may be provided by a hardware device and embodied as software, firmware, hardware, or any combination thereof.

In the example shown in FIG. 2, the sensing circuitry 46 senses bioelectric brain signals of the patient 12 via select combinations of electrodes of the sets of electrodes 24, 26. The sensing circuitry 46 may include circuitry that measures the electrical activity of a particular region, e.g., an anterior nucleus, thalamus or cortex of the brain 28 via select electrodes of the sets of electrodes 24, 26. For treatment of Parkinson's disease, the sensing circuitry 46 may be configured to measure the electrical activity of the subthalamic nucleus (STN), globus pallidus interna (GPi), globus pallidus externa (GPe), and/or other areas of the basal ganglia.

The sensing circuitry 46 may sample the bioelectric brain signal substantially continuously or at regular intervals, such as, but not limited to, a frequency of about 1 Hz to about 1000 Hz, such as about 250 Hz to about 1000 Hz or about 500 Hz to about 1000 Hz. The sensing circuitry 46 includes circuitry for determining a voltage difference between two electrodes of the sets of electrodes 24, 26, which generally indicates the electrical activity within the particular region of the brain 28. One electrode of the sets of electrodes 26, 24 may act as a reference electrode, and, if the sensing circuitry 46 is implanted within the patient 12, a housing of the IMD 16 or the sensing module in examples in which the sensing circuitry 46 is separate from the IMD 16, may include one or more electrodes that may be used to sense bioelectric brain signals.

The processing circuitry 40 may receive the output of the sensing circuitry 46. In some cases, the processing circuitry 40 may apply additional processing to the bioelectrical signals, e.g., convert the output to digital values for processing and/or amplify the bioelectric brain signal. In addition, in some examples, the sensing circuitry 46 or the processing circuitry 40 may filter the signal from the selected electrodes of the sets of electrodes 24, 26 in order to remove undesirable artifacts from the signal, such as noise from cardiac signals generated within the body of the patient 12. Although the sensing circuitry 46 is incorporated into a common outer housing with the stimulation generation circuitry 44 and the processing circuitry 40 in FIG. 2, in other examples, the sensing circuitry 46 is in a separate outer housing from the outer housing of the IMD 16 and communicates with the processing circuitry 40 via wired or wireless communication techniques. In other examples, a bioelectric brain signal may be sensed via external electrodes (e.g., scalp electrodes).

In some examples, the sensing circuitry 46 may include circuitry to tune to and extract a power level of a particular frequency band of a sensed brain signal. Thus, the power level of a particular frequency band of a sensed brain signal may be extracted prior to digitization of the signal by the processing circuitry 40. By tuning to and extracting the power level of a particular frequency band before the signal is digitized, it may be possible to run frequency domain analysis algorithms at a relatively slower rate compared to systems that do not include a circuit to extract a power level of a particular frequency band of a sensed brain signal prior to digitization of the signal. In some examples, the sensing circuitry 46 may include more than one channel to monitor simultaneous activity in different frequency bands, i.e., to extract the power level of more than one frequency band of a sensed brain signal. These frequency bands may include an alpha frequency band (e.g., 8 Hz to 12 Hz), a beta frequency band (e.g., approximately 12 Hz to approximately 35 Hz), a gamma frequency band (e.g., between approximately 35 Hz to approximately 200 Hz), or other frequency bands.

In some examples, the sensing circuitry 46 may include an architecture that merges chopper-stabilization with heterodyne signal processing to support a low-noise amplifier. In some examples, the sensing circuitry 46 may include a frequency selective signal monitor that includes a chopper-stabilized superheterodyne instrumentation amplifier and a signal analysis unit.

A frequency selective signal monitor may utilize a heterodyning, chopper-stabilized amplifier architecture to convert a selected frequency band of a physiological signal to a baseband for analysis. The physiological signal may include a bioelectric brain signal, which may be analyzed in one or more selected frequency bands to detect bioelectric brain signals oscillating at a pathological frequency and, in response, deliver electrical stimulation to modulate the oscillating frequency of the bioelectric brain signals in accordance with some of the techniques described herein. The frequency selective signal monitor may provide a physiological signal monitoring device comprising a physiological sensing element that receives a physiological signal, an instrumentation amplifier comprising a modulator that modulates the signal at a first frequency, an amplifier that amplifies the modulated signal, and a demodulator that demodulates the amplified signal at a second frequency different from the first frequency. A signal analysis unit may analyze a characteristic of the signal in the selected frequency band. The second frequency may be selected such that the demodulator substantially centers a selected frequency band of the signal at a baseband.

In some examples, the sensing circuitry 46 may sense brain signals substantially at the same time that the IMD 16 delivers therapy to the patient 12. In other examples, the sensing circuitry 46 may sense brain signals and the IMD 16 may deliver therapy at different times.

In some examples, the sensing circuitry 46 may monitor one or more physiological parameters of a patient other than that of bioelectric brain signals, which are indicative of a patient disorder, e.g., in combination with the monitored bioelectrical brains signals of the patients. Suitable patient physiological parameters may include, but are not limited to, muscle tone (e.g., as sensed via electromyography (EMG)), eye movement (e.g., as sensed via electroculography (EOG) or EEG), and body temperature. In some examples, patient movement may be monitored via actigraphy. In one example, the processing circuitry 40 may monitor an EMG signal reflective of the muscle tone of the patient 12 to identify physical movement of the patient. Alternatively, or additionally, the processing circuitry 40 may monitor the physical movement of a patient via one or more motion sensors, such as, e.g., one or more single or multi-axis accelerometer devices.

In some examples, the sensing circuitry 46 may monitor one or more physiological parameters of a patient other than that of bioelectric brain signals, which are indicative of symptoms of Parkinson's disease. For examples, the sensing circuitry 46 may monitor one or more parameters indicative of muscle stiffness or movement (slow movement, tremor, and lack of movement) with may correspond to one or more symptoms of Parkinson's disease. Such parameters may be detected by EMG signals, actigraphy, accelerometers signals, and/or other suitable signal. In some examples, in response to the detection of one or more symptoms of Parkinson's disease based on the monitoring of such parameter(s), the IMD 16 may deliver electrical stimulation selected to suppress brain signals oscillating at a frequency associated with the detected symptoms.

The memory 42 may include any volatile or non-volatile media, such as a random access memory (RAM), read only memory (ROM), non-volatile RAM (NVRAM), electrically erasable programmable ROM (EEPROM), flash memory, and the like. The memory 42 may store computer-readable instructions that, when executed by the processing circuitry 40, cause the IMD 16 to perform various functions described herein. The memory 42 may be considered, in some examples, a non-transitory computer-readable storage medium comprising instructions that cause one or more processors, such as, e.g., the processing circuitry 40, to implement one or more of the example techniques described in this disclosure. The term "non-transitory" may indicate that the storage medium is not embodied in a carrier wave or a propagated signal. However, the term "non-transitory" should not be interpreted to mean that the memory 42 is non-movable. As one example, the memory 42 may be removed from the IMD 16, and moved to another device. In certain examples, a non-transitory storage medium may store data that can, over time, change (e.g., in RAM).

The stimulation generation circuitry 44 may represent a single channel or multi-channel stimulation generator. For example, the stimulation generation circuitry 44 may be capable of delivering, a single stimulation pulse, multiple stimulation pulses or a continuous signal at a given time via a single electrode combination or multiple stimulation pulses at a given time via multiple electrode combinations. The stimulation generation circuitry 44 may include independent controllable sources and sinks for each electrode. A switch or other circuitry may be configured to connect and disconnect the sensing circuitry 46 from the stimulation generation circuitry as needed to, for example, prevent delivered stimulation from damaging the sensing circuitry 46. In some examples, however, the stimulation generation circuitry 44 may be configured to deliver multiple channels on a time-interleaved basis. For example, processing circuitry 40 time divide the output of the stimulation generation circuitry 44 across different electrode combinations at different times to deliver multiple programs or channels of stimulation energy to the patient 12.

In accordance with one or more examples of the disclosure, the processing circuitry 40 and/or a processing circuitry of another device (e.g., processing circuitry of the programmer 14) may control the stimulation generation circuitry 44 to generate and deliver electrical stimulation to one or more regions of the brain 28 to modulate the oscillation frequency of bioelectric brain signals in one or more regions of the brain 28. For example, when bioelectric brain signals are oscillating at a pathological frequency within a region of the brain 28, the processing circuitry 40 may control the stimulation generation circuitry 44 to generate and deliver a sequence of pulse bursts to the region of the brain 28 at a pulse burst frequency. In some examples, the pulse burst frequency is similar to or equal to the pathological frequency at which the pathological brain signals are oscillating, but this is not required. In some examples, each pulse burst of the sequence of pulse bursts is associated with a respective intra-burst pulse frequency. Pairs of adjacent pulse bursts in the sequence of pulse bursts may have different intra-burst pulse frequencies. Pairs of adjacent pulse bursts in the sequence of pulse bursts may have intra-burst pulse frequencies that are not factors of one another.

The telemetry circuitry 50 may support wireless communication between the IMD 16 and the programmer 14 or another computing device under the control of the processing circuitry 40. The processing circuitry 40 of the IMD 16 may, for example, transmit bioelectric brain signals, seizure probability metrics for particular sleep stages, a seizure probability profile for the patient 12, and the like via the telemetry circuitry 50 to a telemetry module within the programmer 14 or another external device. The telemetry circuitry 50 in the IMD 16, as well as telemetry modules in other devices and systems described herein, such as the programmer 14, may accomplish communication by radiofrequency (RF) communication techniques. In addition, the telemetry circuitry 50 may communicate with the programmer 14 via proximal inductive interaction of the IMD 16 with the programmer 14. Accordingly, the telemetry circuitry 50 may send information to the programmer 14 on a continuous basis, at periodic intervals, or upon request from the IMD 16 or the programmer 14.

The power source 52 delivers operating power to various components of the IMD 16. The power source 52 may include a small rechargeable or non-rechargeable battery and a power generation circuit to produce the operating power. Recharging may be accomplished through proximal inductive interaction between an external charger and an inductive charging coil within the IMD 16. In some examples, power requirements may be small enough to allow the IMD 16 to utilize patient motion and implement a kinetic energy-scavenging device to trickle charge a rechargeable battery. In other examples, traditional batteries may be used for a limited period of time.

In some examples, the processing circuitry 40 may determine, based on a bioelectric brain signal sensed by the sensing circuitry 46, that the bioelectric brain signal is oscillating at a pathological frequency. A frequency or range of frequencies may represent a pathological frequency or pathological frequency range when oscillations of brain signals at such frequency or frequencies are associated with one or more symptoms of a patient disorder. For example, beta frequency oscillations in the subthalamic nucleus, globus pallidus interna, globus pallidus externa, and/or other areas of the basal ganglia may be associated with one or more motor symptoms including, e.g., rigidity, akenesia, bradykinesia, diskensia, and/or resting tremor. Beta frequency oscillations may represent bioelectric brain signals within a frequency band from 12 Hz to 35 Hz. Consequently, when the processing circuitry 40 identifies beta frequency oscillations above a threshold amplitude, the processing circuitry 40 may determine that pathological brain signals are present in an area of the brain 28 of the patient 12.

In some examples, the IMD 16 may treat one or more symptoms of a patient disorder associated with pathological brain signals treated by reducing or substantially eliminating bioelectric brain signals at such pathological frequencies when such activity occurs. For example, the processing circuitry 40 may control the stimulation generation circuitry 44 to deliver electrical stimulation to an area of the brain 28 of the patient 12 when the processing circuitry 40 detects a pathological brain signal in the area of the brain 28. In some examples, delivering the electrical stimulation to the area of the brain 28 of the patient 12 evokes synaptic depression in order to suppress the detected pathological brain signal in the area of the brain 28. The manifestation of one or more symptoms associated with a patient condition (e.g., Parkinson's disease) may be reduced or substantially eliminated when the IMD 16 evokes synaptic depression in the area of the brain 28 where the pathological brain signal is oscillating.

The IMD 16 may evoke synaptic depression by delivering electrical stimulation including a sequence of pulse bursts to the area of the patient's brain where the pathological brain signals are present. In some examples, the IMD 16 may deliver the sequence of pulse bursts at a pulse burst frequency that matches a frequency of one or more detected pathological brain signals. Additionally, each pulse burst of the sequence of pulse bursts may include a respective intra-burst pulse frequency. Consequently, the "pulse burst frequency" represents a rate in which the IMD 16 delivers the pulse bursts of the sequence of pulse bursts, and the "intra-burst pulse frequency" corresponding to each pulse burst of the sequence of pulse bursts represents a rate in which the IMD 16 delivers the pulses of each respective pulse bursts. In some examples, the IMD 16 may deliver the sequence of pulse bursts so that the pulse burst frequency matches a frequency of one or more detected pathological brain signals, or matches a factor of a frequency of the one or more detected pathological brain signals.

When the IMD 16 delivers the sequence of pulse bursts so that the pulse burst frequency matches a frequency of a detected pathological brain signals, then each pulse burst of the sequence of pulse bursts delivered by the IMD 16 may correspond to a respective cycle of the pathological brain signal, and the IMD 16 may deliver one pulse burst per cycle of the pathological brain signal. For example, when the medical device delivers the sequence of pulse bursts at 20 Hz, the medical device delivers the sequence of pulse bursts at a rate of 20 pulse bursts per second. In some examples, the IMD 16 may align the pulse bursts such that the IMD 16 delivers the pulse bursts substantially at valleys of the pathological brain signal. In some examples, the IMD 16 may align the pulse bursts with valleys of the pathological brain signal such that a first pulse of each pulse burst occurs at a respective valley of the pathological brain signal. In some examples, the IMD 16 may align the pulse bursts with valleys of the pathological brain signal such that a midpoint of each pulse burst occurs at a respective valley of the pathological brain signal. In some examples, the IMD 16 may align the pulse bursts such that the IMD 16 delivers the pulse bursts substantially at peaks of the pathological brain signal. In some examples, the IMD 16 may align the pulse bursts with valleys of the pathological brain signal such that a first pulse of each pulse burst occurs at a respective peak of the pathological brain signal. In some examples, the IMD 16 may align the pulse bursts with valleys of the pathological brain signal such that a midpoint of each pulse burst occurs at a respective peak of the pathological brain signal.

When the processing circuitry 40 controls the stimulation generation circuitry 44 to align the pulse bursts with valleys of the pathological brain signal, the processing circuitry 40 may evoke synaptic depression and suppress the pathological brain signal. By controlling the stimulation generation circuitry 44 to align the pulse bursts with valleys of the pathological signal, the processing circuitry 40 may attenuate an amplitude of the pathological brain signal so the symptoms associated with the pathological brain signal are mitigated or completely eliminated, or the processing circuitry 40 may completely eliminate the pathological brain signal so that symptoms associated with the pathological brain signal are completely eliminated.

In some examples, the processing circuitry 40 may control the stimulation generation circuitry 44 to deliver a sequence of pulse bursts at some multiple (approximately 2 times, approximately 3 times, and/or approximately 0.5 times) of the frequency of a detected pathological brain signal. By delivering the sequence of pulse bursts with a frequency that is a whole multiple of the frequency of the pathological brain signal (e.g., approximately 2 times, approximately 3 times, and so forth), each pulse burst of the sequence of pulse bursts may correspond to a respective event of the pathological brain signal, and more than one pulse burst may correspond to a single cycle of the pathological brain signal. When the IMD 16 delivers the sequence of pulse bursts at some frequency that is a fraction (½ or ¼, for example) of the frequency of a detected pathological brain signal, then not every cycle of the pathological brain signal may correspond to a pulse burst of the sequence of pulse bursts.

The processing circuitry 40 may control the stimulation generation circuitry 44 to deliver the sequence of pulse bursts including pulse bursts of varying frequencies. That is, the processing circuitry 40 may control the stimulation generation circuitry 44 to deliver the sequence of pulse bursts at a pulse burst frequency, wherein each pulse burst of the sequence of pulse bursts is delivered at an intra-burst pulse frequency that is not necessarily the same as intra-burst pulse frequencies of one or more other pulse bursts. For example, a first pulse burst may include a first intra-burst pulse frequency and a second pulse burst may include a second intra-burst pulse frequency that is different than the first intra-burst pulse frequency. In some examples, it may be beneficial for the intra-burst pulse frequency of a pulse burst to be different than the intra-burst pulse frequencies of adjacent pulse bursts in the sequence of pulse bursts. That is, when the sequence of pulse bursts includes a first pulse burst at a first intra-burst pulse frequency, a second pulse burst at a second intra-burst pulse frequency following the first pulse burst, and a third pulse burst at a third intra-burst pulse frequency following the second pulse burst, it may be beneficial for the processing circuitry 40 to control the stimulation generation circuitry 44 to deliver the sequence of pulse bursts so that the first frequency is different than the second frequency and the third frequency is different than the second frequency. Varying the intra-burst pulse frequencies of pulse bursts within the sequence of pulse bursts may prevent the sequence of pulse bursts from entraining the pathological brain signal while still suppressing the pathological brain signal.

Moreover, it may be beneficial for the processing circuitry 40 to control the stimulation generation circuitry 44 to deliver the sequence of pulse bursts so that adjacent pulse bursts are nonharmonic in frequency in order to prevent the sequence of pulse bursts from entraining the bioelectric brain signals. That is, a factor of the intra-burst pulse frequency of one pulse burst may be different than the factors of the intra-burst pulse frequencies of adjacent pulse bursts of the sequence of pulse bursts. For example, when the sequence of pulse bursts includes a first pulse burst at a first intra-burst pulse frequency, a second pulse burst at a second intra-burst pulse frequency following the first pulse burst, and a third pulse burst at a third intra-burst pulse frequency following the second pulse burst, it may be beneficial for the processing circuitry 40 to control the stimulation generation circuitry 44 to deliver the sequence of pulse bursts so that a factor of the first frequency is different than a factor of the second frequency and a factor of the third frequency is different than the factor of the second frequency. When the IMD 16 delivers a sequence of pulse bursts where adjacent pulse bursts have nonharmonic frequencies, the IMD 16 may suppress pathological brain signals. However, the IMD 16 may avoid entraining the pathological brain signals and thus avoid affecting bioelectric brain signals across the brain 28.

The IMD 16 may suppress a pathological brain signal without entraining the pathological brain signal so that electrical stimulation in one area of the brain does not affect brain activity in other areas of the brain as compared with techniques where the medical device does entrain bioelectric brain signals. When a bioelectric brain signal is entrained, electrical stimulation delivered by the IMD 16 may "pull" or "draw" the bioelectric brain signal to match the frequency of the electrical stimulation. When a frequency of the electrical stimulation changes, the frequency of an entrained bioelectric brain signal may also change to match the frequency of the electrical stimulation. Consequently, an entrained brain signal may "follow" a period, frequency, and/or phase of delivered electrical stimulation for a period of time. When bioelectric brain signals follow a change in the period, frequency, and/or phase of electrical stimulation in one area of the brain 28, the period, frequency and/or phase of bioelectric brain signals in other areas of the brain 28 may also follow the change. Consequently, in some examples, it may be beneficial for the IMD 16 to suppress some bioelectric brain signals without entraining these signals, so that the IMD 16 can suppress pathological signals in local areas of the brain without affecting bioelectric brain signals in other areas of the brain through entrainment.

In some examples, the IMD 16 may deliver electrical stimulation therapy to the brain 28 of the patient 12 upon detecting the bioelectric brain signal oscillations at a pathological frequency and/or detecting manifestations of one or more symptoms associated with the pathological brain signal. Additionally, or alternatively, the IMD 16 may deliver electrical stimulation therapy periodically to the brain 28 and not in response detecting pathological brain signals and/or detecting manifestations of one or more symptoms associated with the pathological brain signal. In some examples, the IMD 16 may deliver the electrical stimulation therapy based on patient input. In some examples, the IMD 16 may continuously deliver the electrical stimulation to the brain 28 of the patient 12.

Figure 3:
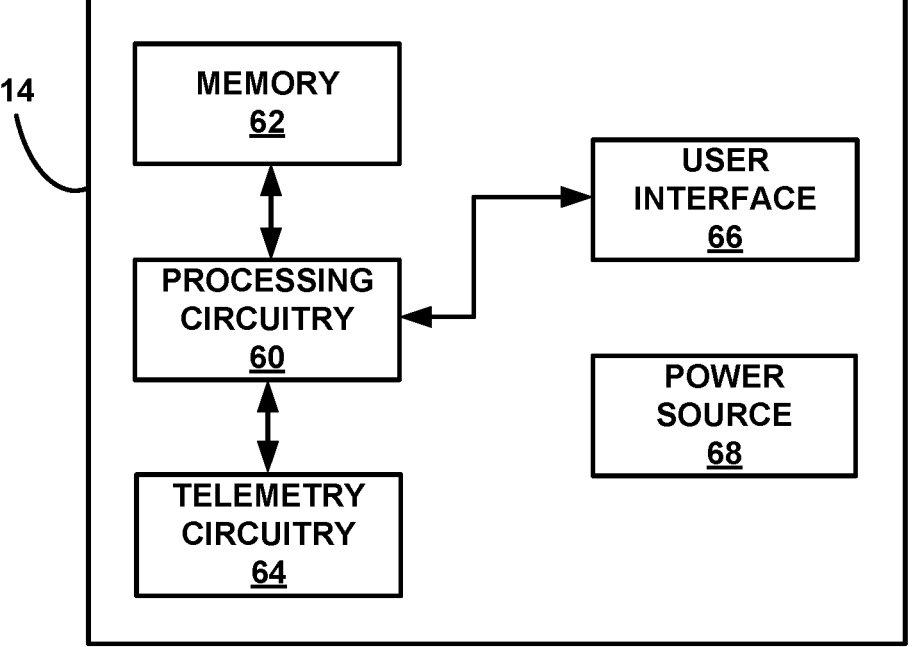
FIG. 3 is a conceptual block diagram of the programmer of FIG. 1, in accordance with one or more techniques of this disclosure.

FIG. 3 is a conceptual block diagram of the programmer 14 of FIG. 1, in accordance with one or more techniques of this disclosure. As seen in FIG. 3, the programmer 14 includes processing circuitry 60, a memory 62, telemetry circuitry 64, a user interface 66, and a power source 68. The processing circuitry 60 controls the user interface 66 and the telemetry circuitry 64, and stores and retrieves information and instructions to and from the memory 62. The programmer 14 may be configured for use as a clinician programmer or a patient programmer. The processing circuitry 60 may comprise any combination of one or more processors including one or more microprocessors, DSPs. ASICs, FPGAs, or other equivalent integrated or discrete logic circuitry. Accordingly, the processing circuitry 60 may include any suitable structure, whether in hardware, software, firmware, or any combination thereof, to perform the functions ascribed herein to the processing circuitry 60.

A user, such as a clinician or the patient 12, may interact with the programmer 14 through the user interface 66. The user interface 66 includes a display (not shown), such as an LCD or LED display or other type of screen, to present information related to treatment of the seizure disorder of the patient 12. The user interface 66 may also include an input mechanism to receive input from the user. The input mechanisms may include, for example, buttons, a keypad (e.g., an alphanumeric keypad), a peripheral pointing device or another input mechanism that allows the user to navigate through user interfaces presented by the processing circuitry 60 of the programmer 14 and provide input.

The memory 62 may include instructions for operating the user interface 66 and the telemetry circuitry 64, and for managing the power source 68. The memory 62 may also store any therapy data retrieved from the IMD 16 during the course of therapy, as well as sensed bioelectric brain signals. The clinician may use this therapy data to determine the progression of the patient condition in order to plan future treatment. The memory 62 may include any volatile or nonvolatile memory, such as RAM, ROM, EEPROM or flash memory. The memory 62 may also include a removable memory portion that may be used to provide memory updates or increases in memory capacities. A removable memory may also allow sensitive patient data to be removed before the programmer 14 is used by a different patient.

The memory 62 may be considered, in some examples, a non-transitory computer-readable storage medium comprising instructions that cause one or more processors, such as, e.g., the processing circuitry 60, to implement one or more of the example techniques described in this disclosure. The term "non-transitory" may indicate that the storage medium is not embodied in a carrier wave or a propagated signal. However, the term "non-transitory" should not be interpreted to mean that the memory 62 is non-movable. As one example, the memory 62 may be removed from the programmer 14, and moved to another device. In certain examples, a non-transitory storage medium may store data that can, over time, change (e.g., in RAM).

Wireless telemetry in the programmer 14 may be accomplished by RF communication or proximal inductive interaction of the programmer 14 with the IMD 16. This wireless communication is possible through the use of the telemetry circuitry 64. Accordingly, the telemetry circuitry 64 may be similar to the telemetry module contained within the IMD 16. In alternative examples, the programmer 14 may be capable of infrared communication or direct communication through a wired connection. In this manner, other external devices may be capable of communicating with the programmer 14 without needing to establish a secure wireless connection.

The power source 68 may deliver operating power to the components of the programmer 14. The power source 68 may include a battery and a power generation circuit to produce the operating power. In some examples, the battery may be rechargeable to allow extended operation.

Figure 4:
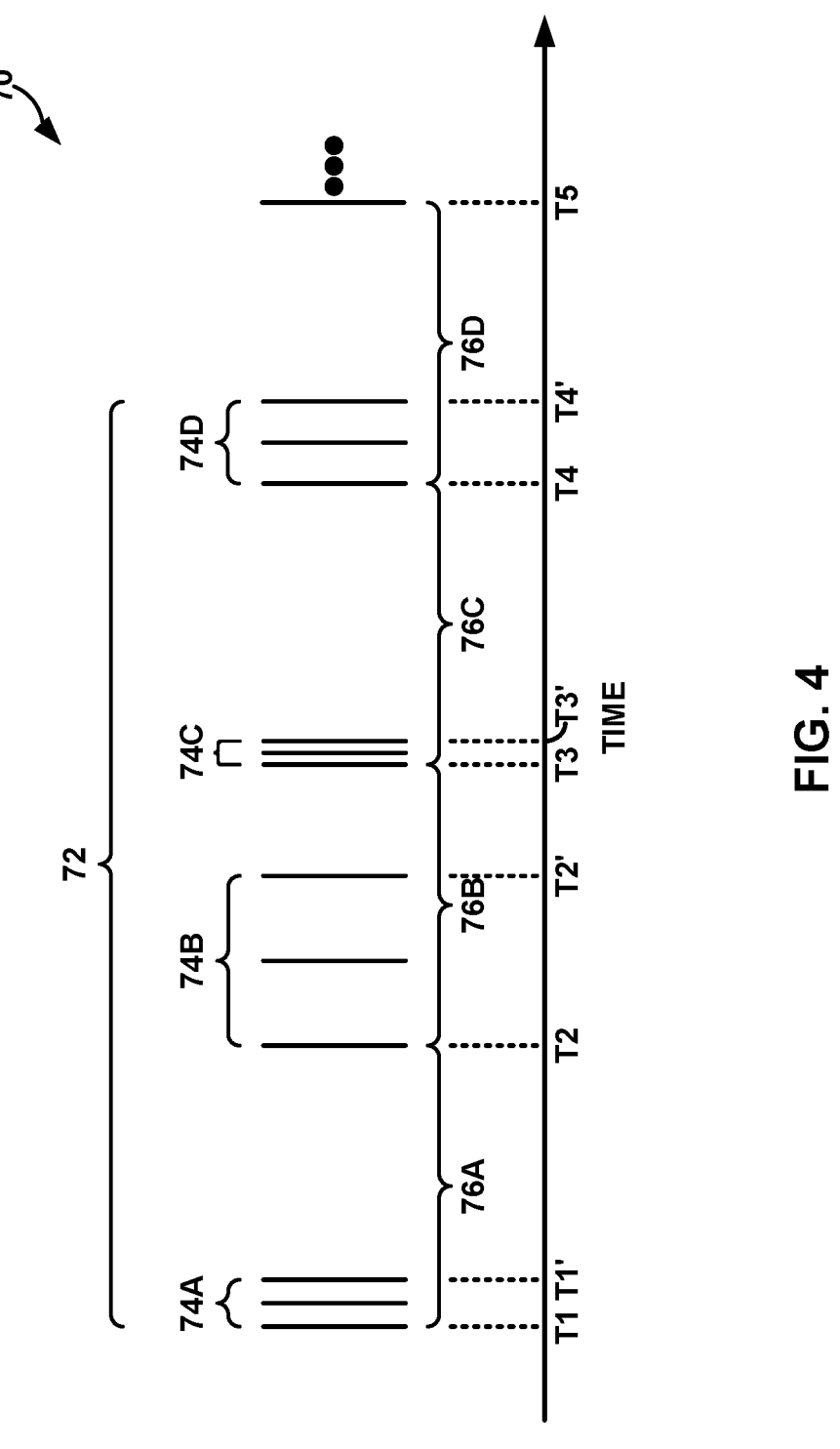
FIG. 4 is a conceptual diagram illustrating an example first timing diagram of a first sequence of pulse bursts, in accordance with one or more techniques of this disclosure.

FIG. 4 is a conceptual diagram illustrating a first timing diagram 70 of a first sequence of pulse bursts 72, in accordance with one or more techniques of this disclosure. As seen in FIG. 4, the first sequence of the pulse bursts 72 includes a set of pulse bursts 74A-74D (collectively, "pulse bursts 74"). Each pulse burst of the set of the pulse bursts 74 may start at a beginning of a respective pulse burst interval of pulse burst intervals 76A-76D. The pulse burst 74A starts at a beginning of the pulse burst interval 76A, the pulse burst 74B starts at a beginning of the pulse burst interval 76B, the pulse burst 74C starts at a beginning of the pulse burst interval 76C, and the pulse burst 74D starts at a beginning of the pulse burst interval 76D.

The processing circuitry 40 may control the stimulation generation circuitry 44 to deliver the first sequence of the pulse bursts 72 so that each pulse burst interval of the pulse burst intervals 76 extends for the same amount of time. That is, the pulse burst interval 76A, the pulse burst interval 76B, the pulse burst interval 76C, and the pulse burst interval 76D may all extend for an equal amount of time. The pulse burst frequency of the first sequence of the pulse bursts 72 may represent an inverse of the amount of time of each of the pulse burst intervals 76. For example, when each pulse burst interval of the pulse burst intervals 76 extends for 50 milliseconds (ms), then the pulse burst frequency is 20 Hz, since the processing circuitry 40 controls the stimulation generation circuitry 44 to deliver the first sequence of the pulse bursts 72 at a rate of 20 pulse bursts per second.

As seen in FIG. 4, each pulse burst of the set of the pulse bursts 74 may correspond to a respective intra-burst pulse frequency. The pulse burst 74A may correspond to a first intra-burst pulse frequency, the pulse burst 74B may correspond to a second intra-burst pulse frequency, the pulse burst 74C may correspond to a third intra-burst pulse frequency, and the pulse burst 74D may correspond to a fourth intra-burst pulse frequency. In one example, the first intra-burst pulse frequency corresponding to the pulse burst 74A is 250 Hz, the second intra-burst pulse frequency corresponding to the pulse burst 74B is 70 Hz, the third intra-burst pulse frequency corresponding to the pulse burst 74C is 500 Hz, and the fourth intra-burst pulse frequency corresponding to the pulse burst 74D is 140 Hz. Consequently, in the example of FIG. 4, each pulse burst of the set of the pulse bursts 74 corresponds to a respective intra-burst pulse frequency that is different than intra-burst pulse frequencies of neighboring pulse bursts and is nonharmonic with intra-burst pulse frequencies of neighboring pulse bursts. For example, the second intra-burst pulse frequency of 70 Hz corresponding to the pulse burst 74B is different than the first intra-burst pulse frequency of 250 Hz corresponding to the pulse burst 74A and is different than the third intra-burst pulse frequency of 500 Hz corresponding to the pulse burst 74C. Additionally, the second intra-burst pulse frequency of 70 Hz corresponding to the pulse burst 74B is nonharmonic with the first intra-burst pulse frequency of 250 Hz corresponding to the pulse burst 74A because 70 Hz is not a factor of 250 Hz, and the second intra-burst pulse frequency of 70 Hz corresponding to the pulse burst 74B is nonharmonic with the intra-burst pulse frequency of 500 Hz corresponding to the pulse burst 74C because 70 Hz is not a factor of 500 Hz.

It may be beneficial for neighboring pulse bursts of the set of the pulse bursts 74 to have different and nonharmonic intra-burst pulse frequencies, so that the first sequence of pulse the bursts 72 can suppress one or more pathological brain signals without entraining the one or more pathological brain signals. By delivering the first sequence of the pulse bursts 72 at the pulse burst frequency, the IMD 16 may suppress the one or more detected pathological brain signals. Delivering the first sequence of the pulse bursts 72 to include the set of the pulse bursts 74 including varying intra-burst pulse frequencies may prevent the first sequence of the pulse bursts 72 from entraining the pathological brain signal. Using varying and nonharmonic intra-burst pulse frequencies prevents the first sequence of the pulse bursts 72 from entraining the pathological brain signal, because the pathological brain signal is less likely to follow the pulse burst frequency when the pulse bursts include pulse bursts of varying and nonharmonic frequencies.

As seen in FIG. 4, the pulse burst 74A extends from time T1 to time T1', the pulse burst 74B extends from time T2 to time T2', the pulse burst 74C extends from time T3 to time T3', and the pulse burst 74D extends from time T4 to time T4'. Additionally, the interval 76A extends from time T1 to time T2, the interval 76B extends from time T2 to time T3, the interval 76C extends from time T3 to time T4, and the interval 76D extends from time T4 to time T5. Since the set of the pulse bursts 74 have varying intra-burst pulse frequencies, the pulse bursts 74 extend for varying amounts of time. For example, a difference between T1 and T1' is less than a difference between T2 and T2', because the intra-burst pulse frequency of the pulse burst 74A is greater than the intra-burst pulse frequency of the pulse burst 74B. Since the interval 76A extends for the same amount of time as the interval 76B, the percentage of the interval 76A covered by the pulse burst 74A is less than the percentage of the interval 76B covered by the pulse burst 74B. Although each pulse burst of the set of the pulse bursts 74 is show as including three pulses, this is not required. In one or mor examples not illustrated in FIG. 4, pulse bursts may include more than three pulses or less than three pulses. Additionally, it is not necessary that every pulse burst in a sequence of pulse bursts have the same number of pulses. In some examples, a pulse burst of a sequence of pulse bursts may have a different number of pulses than one or more other pulse bursts of the sequence of pulse bursts.

In some examples, the processing circuitry 40 may control the stimulation generation circuitry 44 to deliver another sequence of pulse bursts substantially the same as the first sequence of the pulse bursts 72 starting at T5. In some examples, the processing circuitry 40 may control the stimulation generation circuitry 44 to repeat the first sequence of the pulse bursts 72 for a period of time until the IMD 16 detects that the pathological brain signal is suppressed. In response to detecting that the pathological brain signal is suppressed, the processing circuitry 40 may cease delivering the first sequence of the pulse bursts 72 or, if additional therapy is being delivered to the brain, completely cease delivering all electrical stimulation. In some examples, the processing circuitry 40 may control the stimulation generation circuitry 44 to repeat the first sequence of the pulse bursts 72 but leave gaps of time between delivering sequences of pulse bursts. In some examples, the IMD 16 may deliver multiple sequences of pulse bursts, where each sequence of pulse burst is different than other sequences of pulse bursts.

Figure 5:
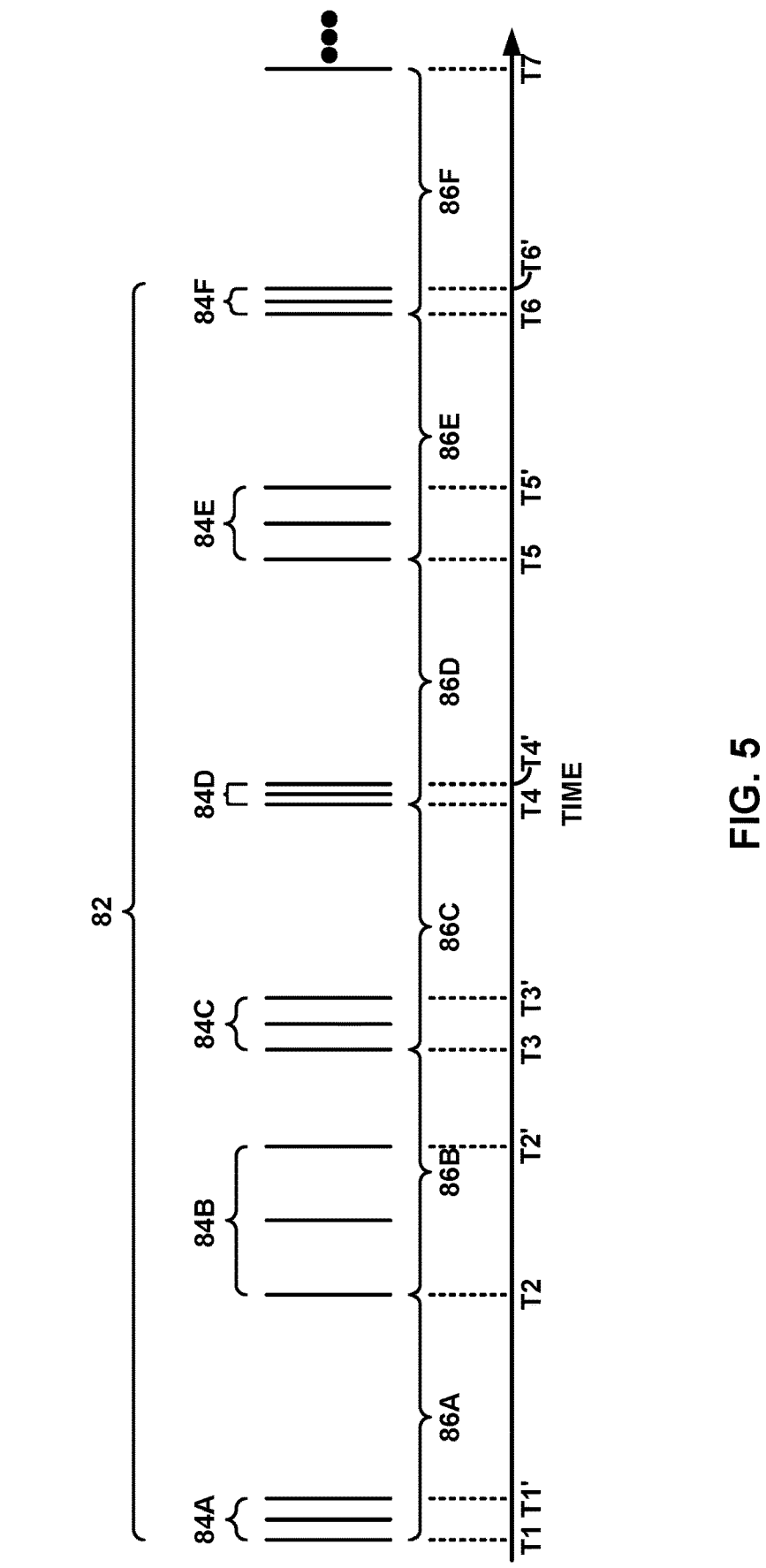
FIG. 5 is a conceptual diagram illustrating a second timing diagram of a second sequence of pulse bursts, in accordance with one or more techniques of this disclosure.

FIG. 5 is a conceptual diagram illustrating a second timing diagram 80 of a second sequence of pulse bursts 82, in accordance with one or more techniques of this disclosure. As seen in FIG. 5, the second sequence of the pulse bursts 82 includes a set of pulse bursts 84A-84F (collectively, "pulse bursts 84"). Each pulse burst of the set of the pulse bursts 84 may start at a beginning of a respective pulse burst interval of pulse burst intervals 86A-86F. The pulse burst 84A starts at a beginning of the pulse burst interval 86A, the pulse burst 84B starts at a beginning of the pulse burst interval 86B, the pulse burst 84C starts at a beginning of the pulse burst interval 86C, the pulse burst 84D starts at a beginning of the pulse burst interval 86D, the pulse burst 84E starts at a beginning of the pulse burst interval 86E, and the pulse burst 84F starts at a beginning of the pulse burst interval 86F.

The second sequence of the pulse bursts 82 is similar to the first sequence of the pulse bursts 72 of FIG. 4, except that the second sequence of the pulse bursts 82 includes six pulse bursts, whereas the first sequence of the pulse bursts 72 includes four pulse bursts. The IMD 16 may deliver the second sequence of the pulse bursts 82 according to any of the techniques described in FIGS. 1-4. As seen in FIG. 5, each pulse burst of the set of the pulse bursts 84 may correspond to a respective intra-burst pulse frequency. The pulse burst 84A may correspond to a first intra-burst pulse frequency, the pulse burst 84B may correspond to a second intra-burst pulse frequency, the pulse burst 84C may correspond to a third intra-burst pulse frequency, the pulse burst 84D may correspond to a fourth intra-burst pulse frequency, the pulse burst 84E may correspond to a fifth intra-burst pulse frequency, and the pulse burst 84F may correspond to a sixth intra-burst pulse frequency. In one example, the first intra-burst pulse frequency corresponding to the pulse burst 84A is 250 Hz, the second intra-burst pulse frequency corresponding to the pulse burst 84B is 70 Hz, the third intra-burst pulse frequency corresponding to the pulse burst 84C is 200 Hz, the fourth intra-burst pulse frequency corresponding to the pulse burst 84D is 500 Hz, the fifth intra-burst pulse frequency corresponding to the pulse burst 84E is 140 Hz, and the sixth intra-burst pulse frequency corresponding to the pulse burst 84F is 250 Hz. Consequently, in the example of FIG. 5, each pulse burst of the set of the pulse bursts 84 corresponds to a respective intra-burst pulse frequency that is different than intra-burst pulse frequencies of neighboring pulse bursts and is nonharmonic with intra-burst pulse frequencies of neighboring pulse bursts.

Figure 6:
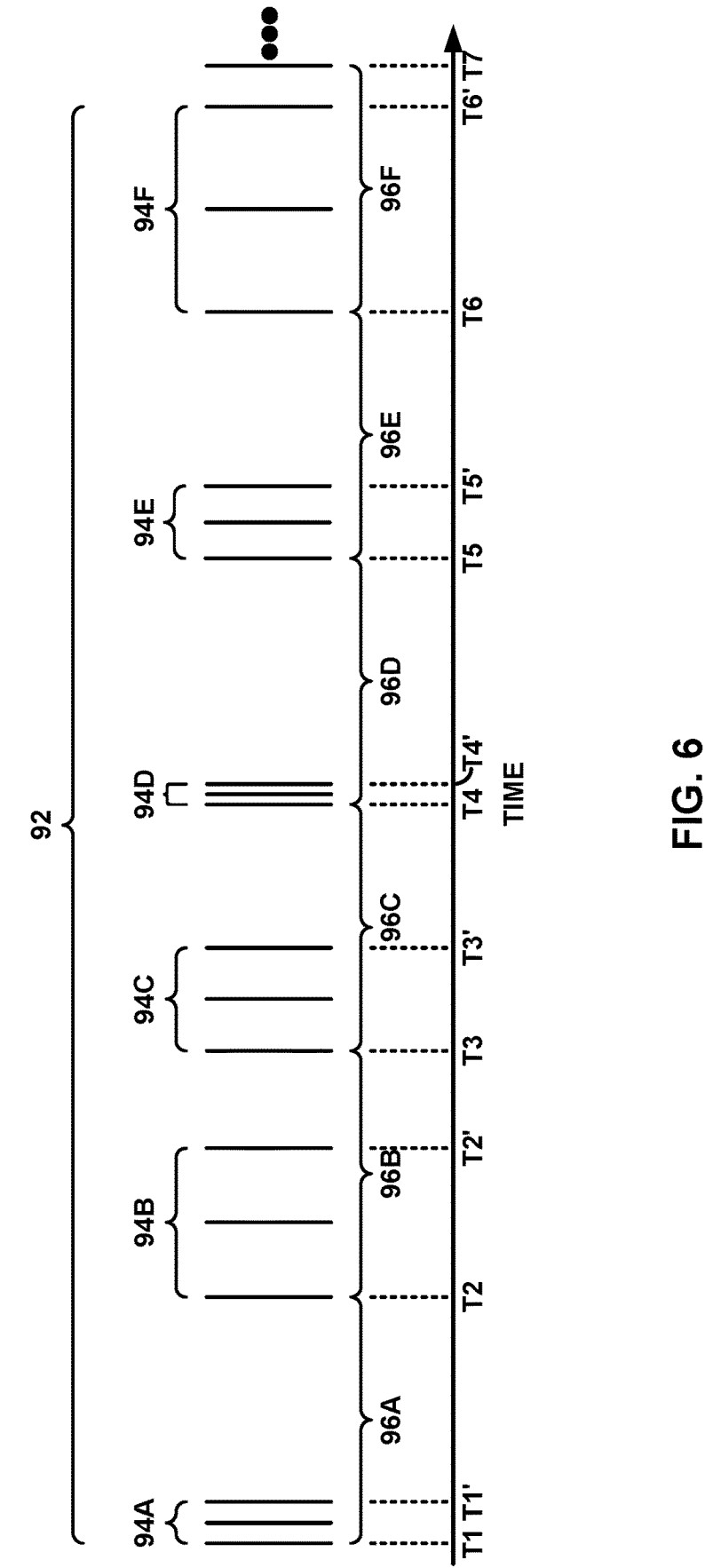
FIG. 6 is a conceptual diagram illustrating a third timing diagram of a third sequence of pulse bursts, in accordance with one or more techniques of this disclosure.

FIG. 6 is a conceptual diagram illustrating a third timing diagram 90 of a third sequence of pulse bursts 92, in accordance with one or more techniques of this disclosure. As seen in FIG. 5, the third sequence of the pulse bursts 92 includes a set of pulse bursts 94A-94F (collectively, "pulse bursts 94"). Each pulse burst of the set of the pulse bursts 94 may start at a beginning of a respective pulse burst interval of pulse burst intervals 96A-96F. The pulse burst 94A starts at a beginning of the pulse burst interval 96A, the pulse burst 94B starts at a beginning of the pulse burst interval 96B, the pulse burst 94C starts at a beginning of the pulse burst interval 96C, the pulse burst 94D starts at a beginning of the pulse burst interval 96D, the pulse burst 94E starts at a beginning of the pulse burst interval 96D, and the pulse burst 94F starts at a beginning of the pulse burst interval 96F.

The third sequence of the pulse bursts 92 is similar to the second sequence of the pulse bursts 82 of FIG. 5, except that intra-burst pulse frequencies of at least some of the pulse bursts 94 may be different than corresponding pulse bursts of the pulse bursts 84 of FIG. 5. The IMD 16 may deliver the third sequence of the pulse bursts 92 according to any of the techniques described in FIGS. 1-5. As seen in FIG. 5, each pulse burst of the set of the pulse bursts 94 may correspond to a respective intra-burst pulse frequency. The pulse burst 94A may correspond to a first intra-burst pulse frequency, the pulse burst 94B may correspond to a second intra-burst pulse frequency, the pulse burst 94C may correspond to a third intra-burst pulse frequency, the pulse burst 94D may correspond to a fourth intra-burst pulse frequency, the pulse burst 94E may correspond to a fifth intra-burst pulse frequency, and the pulse burst 94F may correspond to a sixth intra-burst pulse frequency. In one example, the first intra-burst pulse frequency corresponding to the pulse burst 94A is 250 Hz, the second intra-burst pulse frequency corresponding to the pulse burst 94B is 70 Hz, the third intra-burst pulse frequency corresponding to the pulse burst 94C is 100 Hz, the fourth intra-burst pulse frequency corresponding to the pulse burst 94D is 500 Hz, the fifth intra-burst pulse frequency corresponding to the pulse burst 94E is 140 Hz, and the sixth intra-burst pulse frequency corresponding to the pulse burst 94F is 50 Hz. Consequently, in the example of FIG. 5, each pulse burst of the set of the pulse bursts 94 corresponds to a respective intra-burst pulse frequency that is different than intra-burst pulse frequencies of neighboring pulse bursts and is nonharmonic with intra-burst pulse frequencies of neighboring pulse bursts.

Figure 7:
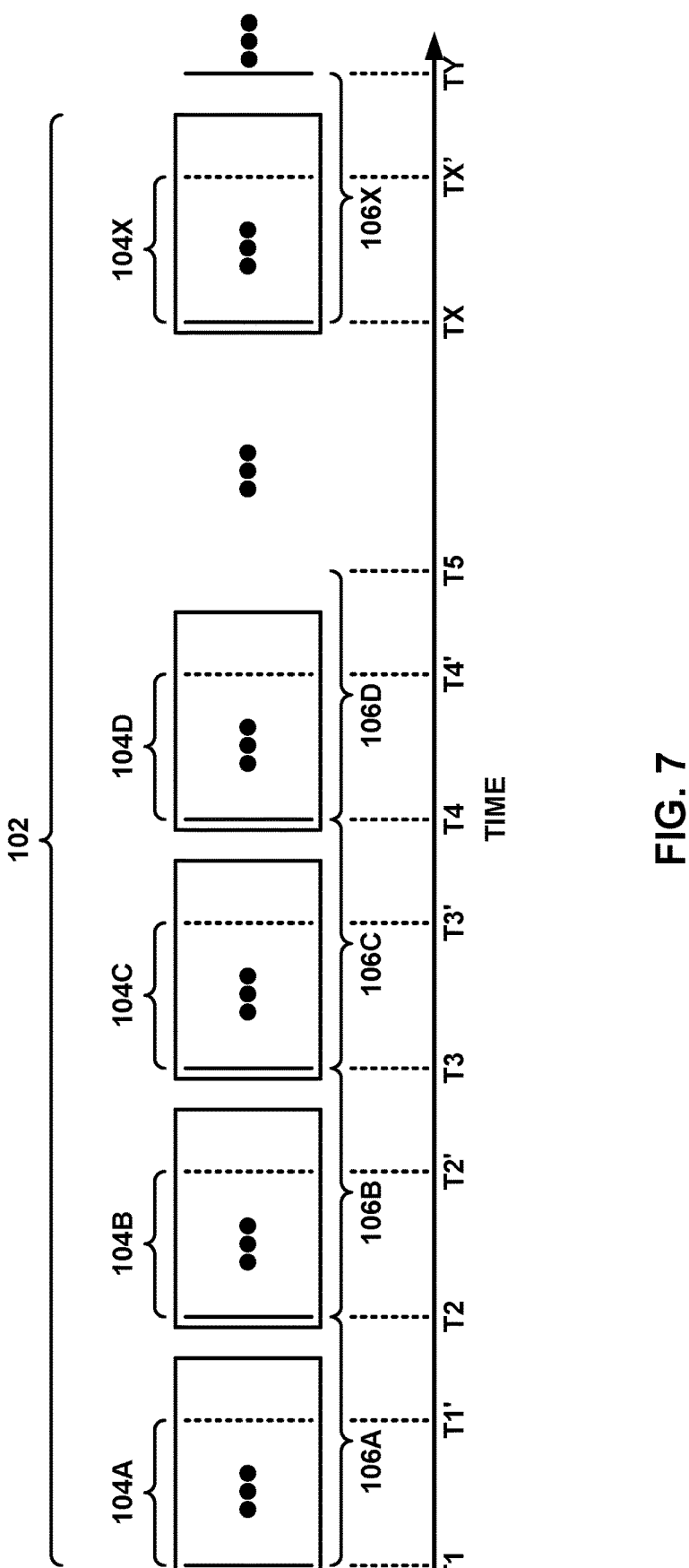
FIG. 7 is a conceptual diagram illustrating a fourth timing diagram of a fourth sequence of pulse bursts, in accordance with one or more techniques of this disclosure.

FIG. 7 is a conceptual diagram illustrating a fourth timing diagram 100 of a fourth sequence of pulse bursts 102, in accordance with one or more techniques of this disclosure. As seen in FIG. 7, the fourth sequence of the pulse bursts 102 includes a set of pulse bursts 104A-104F (collectively, "pulse bursts 104"). Each pulse burst of the set of the pulse bursts 104 may start at a beginning of a respective pulse burst interval of pulse burst intervals 106A-106F. The pulse burst 104A starts at a beginning of the pulse burst interval 106A, the pulse burst 104B starts at a beginning of the pulse burst interval 106B, the pulse burst 104C starts at a beginning of the pulse burst interval 106C, the pulse burst 104D starts at a beginning of the pulse burst interval 106D, the pulse burst 104E starts at a beginning of the pulse burst interval 106E, and the pulse burst 104F starts at a beginning of the pulse burst interval 106F.

The first sequence of the pulse bursts 72 of FIG. 4, the second sequence of the pulse bursts 82 of FIG. 5, and the third sequence of the pulse bursts 92 of FIG. 6 are examples of pulse burst sequences which the IMD 16 may deliver to the brain 28 of the patient 12, but the techniques described herein are not limited to these examples. The IMD 16 may deliver the fourth sequence of the pulse bursts 102 according to any of the techniques described in FIGS. 1-5. Additionally, or alternatively, the IMD 16 may deliver other sequences of pulse bursts. For example, the fourth sequence of the pulse bursts 102 includes the set of the pulse bursts 104.

Although FIG. 7 illustrates the set of the pulse bursts 104 as including five pulse bursts, the set of the pulse bursts 104 may include more than five pulse bursts or less than five pulse bursts. Each pulse burst of the set of the pulse bursts 104 may include two or more pulses. For example, the pulse burst 104A may include a first pulse delivered at time T1 and a second pulse delivered at time T1'. In some examples, the pulse burst 104A may include one or more intervening pulses between the first pulse and the second pulse delivered between time T1 and time T1'. The IMD 16 may deliver the pulse burst 104A at a first pulse burst frequency. An amount of time between T1 and T1' may vary depending on a number of pulses in the pulse burst 104A and the first intra-burst pulse frequency of the pulse burst 104A. The pulse burst 104B may include a first pulse delivered at time T2 and a second pulse delivered at time T2'. In some examples, the pulse burst 104B may include one or more intervening pulses delivered between time T2 and time T2'. The IMD 16 may deliver the pulse burst 104B at a second pulse burst frequency. An amount of time between T2 and T2' may vary depending on a number of pulses in the pulse burst 104A and the first intra-burst pulse frequency of the pulse burst 104A. The pulse burst 104C, the pulse burst 104D, and the pulse burst 104X may each be associated with a respective intra-burst pulse frequency and a respective number of two or more pulses. As such, the pulse bursts 104 may represent many different example pulse bursts. In some examples, each pulse burst of the set of the pulse bursts 104 has a uniform pulse frequency (e.g., an interval between each pair of consecutive pulses in a pulse burst is equal to the interval between each other pair of consecutive pulses in the pulse burst.

In some examples, it may be beneficial for neighboring pulse bursts of the set of the pulse bursts 104 to have different and nonharmonic intra-burst pulse frequencies, so that the fourth sequence of the pulse bursts 102 can suppress one or more pathological brain signals without entraining the one or more pathological brain signals. By delivering the fourth sequence of the pulse bursts 102 at a pulse burst frequency, the IMD 16 may suppress the one or more detected pathological brain signals. Delivering the fourth sequence of the pulse bursts 102 to include the set of the pulse bursts 104 including varying intra-burst pulse frequencies may prevent the fourth sequence of the pulse bursts 102 from entraining the pathological brain signal. Using varying and nonharmonic intra-burst pulse frequencies prevents the fourth sequence of the pulse bursts 102 from entraining the pathological brain signal, because the pathological brain signal is less likely to follow the pulse burst frequency when the pulse bursts include pulse bursts of varying and nonharmonic frequencies. In some examples, the IMD 16 may deliver more than one sequence of pulse bursts consecutively. In some examples, the IMD 16 may cycle between delivering one or more sequences of pulse bursts and pausing stimulation delivery.

Figure 8:
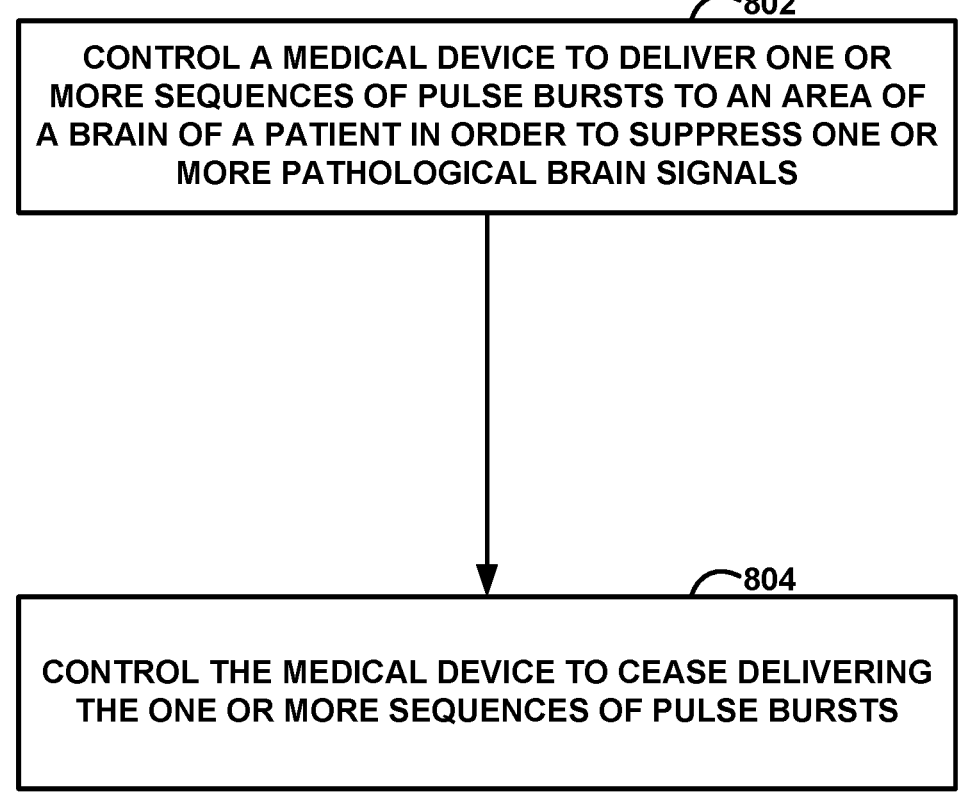
FIG. 8 is a flow diagram illustrating an example operation for controlling the IMD to deliver stimulation with one or more patterns configured to suppress one or more pathological brain signals, in accordance with one or more techniques of this disclosure.

FIG. 8 is a flow diagram illustrating an example operation for controlling the IMD 16 to deliver stimulation with one or more patterns configured to suppress one or more pathological brain signals, in accordance with one or more techniques of this disclosure. FIG. 8 is described with respect to the programmer 14 and the IMD 16 of FIGS. 1-3. However, the techniques of FIG. 8 may be performed by different components of the programmer 14 and the IMD 16, or by additional or alternative medical devices.

The processing circuitry 40 of the IMD 16 may control the stimulation generation circuitry 44 of the IMD 16 to deliver one or more sequences of pulse bursts to an area of the brain 28 of the patient 12 in order to suppress one or more pathological brain signals (802). In some examples, the processing circuitry 40 may detect the one or more pathological brain signals or detect one or more symptoms associated with the one or more pathological brain signals, such that the processing circuitry 40 determines the pulse burst frequency and/or intra-burst pulse frequencies for each burst based on one or more detected pathological frequencies of the patient. However, this sensing feature is not required for all examples. In some examples, the processing circuitry 40 may control the stimulation generation circuitry 44 to deliver a sequence of pulse bursts, where a frequency of each pulse burst of the sequence of pulse bursts is different than a frequency of adjacent pulse bursts of the sequence of pulse bursts. By delivering the sequence of pulse bursts to have pulse bursts of varying frequencies, the IMD 16 may suppress the one or more pathological signals without entraining the one or more pathological brain signals. Additionally, or alternatively, the processing circuitry 40 may control the stimulation generation circuitry 44 to deliver the sequence of pulse bursts so that a frequency of each pulse burst of the sequence of pulse bursts is not harmonic with a frequency of each adjacent pulse burst of the sequence of pulse bursts. By delivering adjacent pulse bursts that are nonharmonic in frequency, the IMD 16 may further prevent the sequence of pulse bursts from entraining the pathological brain signals while suppressing the pathological brain signals.

The processing circuitry 40 may control the stimulation generation circuitry 44 to cease delivering the one or more sequences of pulse bursts (808). In some examples, the processing circuitry 40 may control the stimulation generation circuitry 44 to cease delivering the one or more sequences of pulse bursts based on determining that the one or more pathological brain signals are suppressed, but this is not required. The IMD 16 may cease delivering the one or more sequences of pulse bursts when a predetermined amount of time elapses, or in response to a user input to the programmer 14 to cease delivering electrical stimulation. The IMD 16 may restart stimulation according to the one or more sequencies of pulse bursts at a later scheduled time or in response to detecting pathological brain signals.

Figure 9:
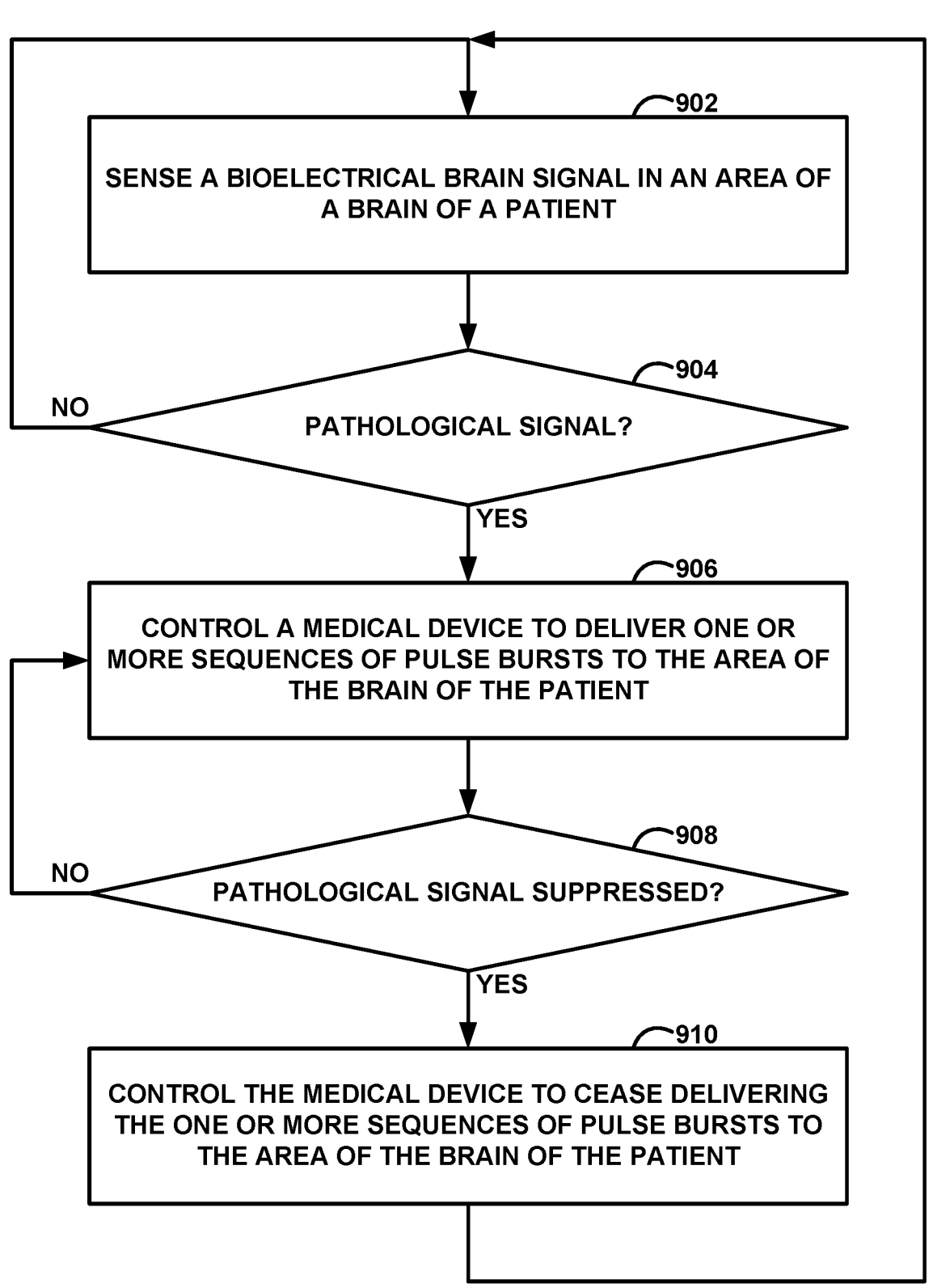
FIG. 9 is a flow diagram illustrating an example operation for detecting one or more pathological brain signals, and controlling the IMD to deliver stimulation with one or more patterns configured to suppress the one or more pathological brain signals, in accordance with one or more techniques of this disclosure.

FIG. 9 is a flow diagram illustrating an example operation for detecting one or more pathological brain signals, and controlling the IMD 16 to deliver stimulation with one or more patterns configured to suppress the one or more pathological brain signals, in accordance with one or more techniques of this disclosure. FIG. 9 is described with respect to the programmer 14 and the IMD 16 of FIGS. 1-3. However, the techniques of FIG. 9 may be performed by different components of the programmer 14 and the IMD 16, or by additional or alternative medical devices.

The sensing circuitry 46 of the IMD 16 is configured to sense a bioelectric brain signal in an area of the brain 28 of the patient 12. (902) The processing circuitry 40 may receive the sensed bioelectric brain signal from the sensing circuitry 46. The processing circuitry 40 may determine whether the bioelectric brain signal represents a pathological brain signal (904). In some examples, the processing circuitry 40 may analyze any one or combination of a frequency of the bioelectric brain signal, an amplitude of the bioelectric brain signal, a phase of the bioelectric brain signal in order to determine whether the bioelectric brain signal represents a pathological brain signal. For example, bioelectric brain signals oscillating in the beta frequency range (e.g., from 12 Hz to 35 Hz) in the subthalamic nucleus, globus pallidus interna, globus pallidus externa, and/or other areas of the basal ganglia may be associated with one or more motor symptoms including, e.g., rigidity, akenesia, bradykinesia, diskensia, and/or resting tremor. Consequently, the processing circuitry 40 may determine that these bioelectric brain signals oscillating in the beta frequency range represent pathological brain signals.

Based on determining that the sensed bioelectric brain signal does not represent a pathological brain signal ("NO" branch of block 904), the processing circuitry 40 may control the sensing circuitry 46 to continue sensing bioelectric brain signals. Based on determining that the sensed bioelectric brain signal represents a pathological brain signal ("YES" branch of block 904), the processing circuitry 40 may control the stimulation generation circuitry 44 to deliver one or more sequences of pulse bursts to the area of the brain 28 of the patient 12 where the sensing circuitry 46 sensed the pathological brain signal (906). In some examples, the processing circuitry 40 may control the stimulation generation circuitry 44 to deliver a sequence of pulse bursts, where a frequency of each pulse burst of the sequence of pulse bursts is different than a frequency of adjacent pulse bursts of the sequence of pulse bursts. By delivering the sequence of pulse bursts to have pulse bursts of varying frequencies, the IMD 16 may suppress the one or more pathological signals without entraining the one or more pathological brain signals. Additionally, or alternatively, the processing circuitry 40 may control the stimulation generation circuitry 44 to deliver the sequence of pulse bursts so that a frequency of each pulse burst of the sequence of pulse bursts is nonharmonic with a frequency of each adjacent pulse burst of the sequence of pulse bursts. By delivering adjacent pulse bursts that are nonharmonic in frequency, the IMD 16 may further prevent the sequence of pulse bursts from entraining the pathological brain signals while suppressing the pathological brain signals.

The processing circuitry 40 may determine whether the sensed pathological brain signal is suppressed (908). In some examples, to determine whether the sensed pathological brain signal is suppressed, the processing circuitry 40 may compare a current amplitude of the pathological brain signal with an amplitude of the pathological brain signal prior to delivery of the one or more sequences of pulse bursts. When the current amplitude is less than the amplitude prior to delivery of electrical stimulation by more than a threshold difference, then the processing circuitry 40 may determine that the sensed pathological brain signal is suppressed. In some examples, the processing circuitry 40 may determine that the sensed pathological brain signal is suppressed when the pathological brain signal is no longer detectable by the IMD 16.

Based on determining that the sensed pathological brain signal is not suppressed ("NO" branch of block 908), the processing circuitry 40 may control the stimulation generation circuitry 44 to continue delivering the one or more sequences of pulse bursts. Based on determining that the sensed pathological brain signal is suppressed ("YES" branch of block 908), the processing circuitry 40 may control the stimulation generation circuitry 44 to cease delivering the one or more sequences of pulse bursts to the area of the brain 28 of the patient 12 (910).

The following examples are example systems, devices, and methods described herein.

Example 1: A system comprising: processing circuitry configured to: receive information representative of a bioelectric brain signal recorded from a brain of a patient; determine, based on the information, at least one pathological frequency of the bioelectric brain signal; select, based on the at least one pathological frequency, a sequence of pulse bursts at a pulse burst frequency, the sequence of pulse bursts at least partially defining electrical stimulation deliverable to an area of a brain of a patient, wherein adjacent pulse bursts within the sequence comprise different intra-burst pulse frequencies; and control a medical device to deliver the electrical stimulation comprising the sequence of pulse bursts to the area of the brain of the patient.

Example 2: The system of example 1, wherein by delivering the electrical stimulation to the brain of the patient, the processing circuitry evokes synaptic depression in order to suppress the bioelectric brain signal in the area of the brain of the patient.

Example 3: The system of any of examples 1-2, wherein an intra-burst pulse frequency of each pulse burst of the sequence of pulse bursts is nonharmonic with an intra-burst pulse frequency of each adjacent pulse burst of the sequence of pulse bursts.

Example 4: The system of any of examples 1-3, wherein the pulse burst frequency matches the at least one pathological frequency of the bioelectric brain signal.

Example 5: The system of example 4, wherein to select the pulse burst frequency based on the bioelectric brain signal, the processing circuitry is configured to select the pulse burst frequency so that each pulse burst of the sequence of pulse bursts aligns with a feature of a respective cycle of the bioelectric brain signal.

Example 6: The system of example 5, wherein each pulse burst of the sequence of pulse bursts aligns with a valley of the bioelectric brain signal.

Example 7: The system of any of examples 1-6, wherein an intra-burst pulse frequency of each pulse burst of the sequence of pulse bursts is within a range from 70 Hertz (Hz) to 500 Hz.

Example 8: The system of any of examples 1-7, wherein the sequence of pulse bursts includes a first pulse burst having an intra-burst first pulse frequency of 250 Hz, a second pulse burst having a second intra-burst pulse frequency of 70 Hz, a third pulse burst having a third intra-burst pulse frequency of 500 Hz, and fourth pulse burst having a fourth intra-burst pulse frequency of 70 Hz.

Example 9: The system of example 8, wherein the range of pathological frequencies includes a beta frequency band extending within a range from 12 Hz to 35 Hz.

Example 10: The system of any of examples 1-9, wherein the processing circuitry is further configured to: determine, based on receiving the information representative of the bioelectric brain signal subsequent to delivering the electrical stimulation, that the pathological brain signal is suppressed; and control the medical device to cease delivering the electrical stimulation to the area of the brain of the patient based on determining that the pathological brain signal is suppressed.

Example 11: The system of any of examples 1-10, wherein the medical device comprises an implantable medical device.

Example 12: A method comprising: receiving, by processing circuitry, information representative of a bioelectric brain signal recorded from a brain of a patient; determining, by the processing circuitry and based on the information, at least one pathological frequency of the bioelectric brain signal; selecting, by processing circuitry and based on the at least one pathological frequency, a sequence of pulse bursts at a pulse burst frequency, the sequence of pulse bursts at least partially defining electrical stimulation deliverable to an area of a brain of a patient, wherein adjacent pulse bursts within the sequence comprise different intra-burst pulse frequencies; and controlling, by the processing circuitry, a medical device to deliver the electrical stimulation comprising the sequence of pulse bursts to the area of the brain of the patient.

Example 13: The method of example 12, wherein delivering the electrical stimulation to the brain of the patient evokes synaptic depression in order to suppress the bioelectric brain signal in the area of the brain of the patient.

Example 14: The method of any of examples 12-13, wherein an intra-burst pulse frequency of each pulse burst of the sequence of pulse bursts is nonharmonic with an intra-burst pulse frequency of each adjacent pulse burst of the sequence of pulse bursts.

Example 15: The method of any of examples 12-14, wherein the pulse burst frequency matches the at least one pathological frequency of the bioelectric brain signal.

Example 16: The method of example 15, wherein selecting the pulse burst frequency based on the bioelectric brain signal comprises selecting the pulse burst frequency so that each pulse burst of the sequence of pulse bursts aligns with a feature of a respective cycle of the bioelectric brain signal.

Example 17: The method of example 16, wherein each pulse burst of the sequence of pulse bursts aligns with a valley of the bioelectric brain signal.

Example 18: The method of any of examples 12-17, wherein an intra-burst pulse frequency of each pulse burst of the sequence of pulse bursts is within a range from 70 Hertz (Hz) to 500 Hz.

Example 19: The method of any of examples 12-18, further comprising: determining, based on receiving the information representative of the bioelectric brain signal subsequent to delivering the electrical stimulation, that the pathological brain signal is suppressed; and controlling the medical device to cease delivering the electrical stimulation to the area of the brain of the patient based on determining that the pathological brain signal is suppressed.

Example 20: A computer-readable medium comprising instructions that, when executed by a processor, causes the processor to: receive information representative of a bioelectric brain signal recorded from a brain of a patient; determine, based on the information, at least one pathological frequency of the bioelectric brain signal; select, based on the at least one pathological frequency, a sequence of pulse bursts at a pulse burst frequency, the sequence of pulse bursts at least partially defining electrical stimulation deliverable to an area of a brain of a patient, wherein adjacent pulse bursts within the sequence comprise different intra-burst pulse frequencies; and control a medical device to deliver the electrical stimulation comprising the sequence of pulse bursts to the area of the brain of the patient.

For aspects implemented in software, at least some of the functionality ascribed to the systems and devices described in this disclosure may be embodied as instructions on a computer-readable storage medium such as RAM, DRAM, SRAM, FRAM, magnetic discs, optical discs, flash memory, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A system comprising:
processing circuitry configured to:
    receive information representative of a bioelectric brain signal recorded from a brain of a patient;
    determine, based on the information, at least one pathological frequency of the bioelectric brain signal;
    select, based on the at least one pathological frequency, a sequence of pulse bursts at a pulse burst frequency, the sequence of pulse bursts at least partially defining electrical stimulation deliverable to an area of the brain of the patient, wherein adjacent pulse bursts within the sequence comprise different intra-burst pulse frequencies; and
    control a medical device to deliver the electrical stimulation comprising the sequence of pulse bursts to the area of the brain of the patient.

2. The system of claim 1, wherein by delivering the electrical stimulation to the brain of the patient, the processing circuitry evokes synaptic depression in order to suppress the bioelectric brain signal in the area of the brain of the patient.

3. The system of claim 1, wherein an intra-burst pulse frequency of each pulse burst of the sequence of pulse bursts is nonharmonic with an intra-burst pulse frequency of each adjacent pulse burst of the sequence of pulse bursts.

4. The system of claim 1, wherein the pulse burst frequency matches the at least one pathological frequency of the bioelectric brain signal.

5. The system of claim 4, wherein to select the pulse burst frequency based on the bioelectric brain signal, the processing circuitry is configured to select the pulse burst frequency so that each pulse burst of the sequence of pulse bursts aligns with a feature of a respective cycle of the bioelectric brain signal.

6. The system of claim 5, wherein each pulse burst of the sequence of pulse bursts aligns with a valley of the bioelectric brain signal.

7. The system of claim 1, wherein an intra-burst pulse frequency of each pulse burst of the sequence of pulse bursts is within a range from 70 Hertz (Hz) to 500 Hz.

8. The system of claim 1, wherein the sequence of pulse bursts includes a first pulse burst having an intra-burst first pulse frequency of 250 Hz, a second pulse burst having a second intra-burst pulse frequency of 70 Hz, a third pulse burst having a third intra-burst pulse frequency of 500 Hz, and fourth pulse burst having a fourth intra-burst pulse frequency of 70 Hz.

9. The system of claim 8, wherein the range of pathological frequencies includes a beta frequency band extending within a range from 12 Hz to 35 Hz.

10. The system of claim 1, wherein the processing circuitry is further configured to:
    determine, based on receiving the information representative of the bioelectric brain signal subsequent to delivering the electrical stimulation, that the pathological brain signal is suppressed; and
    control the medical device to cease delivering the electrical stimulation to the area of the brain of the patient based on determining that the pathological brain signal is suppressed.

11. The system of claim 1, wherein the medical device comprises an implantable medical device.

12. A method comprising:
    receiving, by processing circuitry, information representative of a bioelectric brain signal recorded from a brain of a patient;
    determining, by the processing circuitry and based on the information, at least one pathological frequency of the bioelectric brain signal;
    selecting, by processing circuitry and based on the at least one pathological frequency, a sequence of pulse bursts at a pulse burst frequency, the sequence of pulse bursts at least partially defining electrical stimulation deliverable to an area of the brain of the patient, wherein adjacent pulse bursts within the sequence comprise different intra-burst pulse frequencies; and
    controlling, by the processing circuitry, a medical device to deliver the electrical stimulation comprising the sequence of pulse bursts to the area of the brain of the patient.

13. The method of claim 12, wherein delivering the electrical stimulation to the brain of the patient evokes synaptic depression in order to suppress the bioelectric brain signal in the area of the brain of the patient.

14. The method of claim 12, wherein an intra-burst pulse frequency of each pulse burst of the sequence of pulse bursts is nonharmonic with an intra-burst pulse frequency of each adjacent pulse burst of the sequence of pulse bursts.

15. The method of claim 12, wherein the pulse burst frequency matches the at least one pathological frequency of the bioelectric brain signal.

16. The method of claim 15, wherein selecting the pulse burst frequency based on the bioelectric brain signal comprises selecting the pulse burst frequency so that each pulse burst of the sequence of pulse bursts aligns with a feature of a respective cycle of the bioelectric brain signal.

17. The method of claim 16, wherein each pulse burst of the sequence of pulse bursts aligns with a valley of the bioelectric brain signal.

18. The method of claim 12, wherein an intra-burst pulse frequency of each pulse burst of the sequence of pulse bursts is within a range from 70 Hertz (Hz) to 500 Hz.

19. The method of claim 12, further comprising:
    determining, based on receiving the information representative of the bioelectric brain signal subsequent to delivering the electrical stimulation, that the pathological brain signal is suppressed; and
    controlling the medical device to cease delivering the electrical stimulation to the area of the brain of the patient based on determining that the pathological brain signal is suppressed.

20. A computer-readable medium comprising instructions that, when executed by a processor, causes the processor to:

receive information representative of a bioelectric brain signal recorded from a brain of a patient;

determine, based on the information, at least one pathological frequency of the bioelectric brain signal;

select, based on the at least one pathological frequency, a sequence of pulse bursts at a pulse burst frequency, the sequence of pulse bursts at least partially defining electrical stimulation deliverable to an area of the brain of the patient, wherein adjacent pulse bursts within the sequence comprise different intra-burst pulse frequencies; and control a medical device to deliver the electrical stimulation comprising the sequence of pulse bursts to the area of the brain of the patient.

\* \* \* \* \*